United States Patent
Chang

(10) Patent No.: US 11,191,743 B2
(45) Date of Patent: Dec. 7, 2021

(54) MODULATORS OF ZINC ACTIVATED CATION CHANNEL

(71) Applicant: Dignity Health, Phoenix, AZ (US)

(72) Inventor: Yongchang Chang, Glendale, AZ (US)

( * ) Notice: Subject to any disclaimer, the term of this patent is extended or adjusted under 35 U.S.C. 154(b) by 0 days.

(21) Appl. No.: 16/068,814

(22) PCT Filed: Jan. 11, 2017

(86) PCT No.: PCT/US2017/013015
§ 371 (c)(1),
(2) Date: Jul. 9, 2018

(87) PCT Pub. No.: WO2017/123633
PCT Pub. Date: Jul. 20, 2017

(65) Prior Publication Data
US 2019/0022121 A1   Jan. 24, 2019

Related U.S. Application Data

(60) Provisional application No. 62/277,422, filed on Jan. 11, 2016.

(51) Int. Cl.
| | | |
|---|---|---|
| *A61K 31/185* | (2006.01) | |
| *A61K 31/7076* | (2006.01) | |
| *A61K 31/138* | (2006.01) | |
| *A61K 31/5375* | (2006.01) | |
| *A61K 31/55* | (2006.01) | |
| *A61K 31/727* | (2006.01) | |
| *C07K 14/705* | (2006.01) | |
| *A61K 31/365* | (2006.01) | |
| *A61K 45/06* | (2006.01) | |
| *A61P 25/24* | (2006.01) | |
| *A61P 35/00* | (2006.01) | |
| *A61K 31/41* | (2006.01) | |
| *A61K 31/5415* | (2006.01) | |
| *C12Q 1/6883* | (2018.01) | |
| *C12Q 1/6886* | (2018.01) | |

(52) U.S. Cl.
CPC .......... *A61K 31/185* (2013.01); *A61K 31/138* (2013.01); *A61K 31/365* (2013.01); *A61K 31/41* (2013.01); *A61K 31/5375* (2013.01); *A61K 31/5415* (2013.01); *A61K 31/55* (2013.01); *A61K 31/7076* (2013.01); *A61K 31/727* (2013.01); *A61K 45/06* (2013.01); *A61P 25/24* (2018.01); *A61P 35/00* (2018.01); *C07K 14/705* (2013.01); *C12Q 1/6883* (2013.01); *C12Q 1/6886* (2013.01)

(58) Field of Classification Search
None
See application file for complete search history.

(56) References Cited

U.S. PATENT DOCUMENTS

| | | | | |
|---|---|---|---|---|
| 8,399,018 B2 * | 3/2013 | Lichter | ................ | A61K 9/0019 |
| | | | | 424/484 |
| 2004/0248245 A1 * | 12/2004 | Kirkness | ................ | C07H 21/04 |
| | | | | 435/69.1 |

OTHER PUBLICATIONS

Jarvis, M. F., (2002). A-317491, a novel potent and selective non-nucleotide antagonist of P2X3 and P2X2/3 receptors, reduces chronic inflammatory and neuropathic pain in the rat. Proceedings of the National Academy of Sciences, 99(26), 17179-17184. (Year: 2002).*

Dellal, S. S., & Hume, R. I. (2012). Covalent modification of mutant rat P2X2 receptors with a thiol-reactive fluorophore allows channel activation by zinc or acidic pH without ATP. PloS one, 7(10), e47147. (Year: 2012).*

* cited by examiner

*Primary Examiner* — Dale R Miller

(57) ABSTRACT

Various embodiments disclosed herein include methods of modulating the function of Zinc Activated Cation Channel (ZACN) in a subject comprising: administering to the subject a pharmaceutically effective dosage of ATP, a purinergic compound, red or blue dye, heparin or heparin analog, desipramine, reboxetine, and/or tomoxetine; and modulating the function of ZACN in the subject. Various embodiments disclosed herein also include methods of treating a disease in a subject comprising: administering to the subject a pharmaceutically effective dosage of a compound capable of modulating the function of the Zinc Activated Cation Channel (ZACN), and treating the disease.

8 Claims, 23 Drawing Sheets

CD4⁺CD25⁺ cells: 45.3%    Foxp3⁺ cells : 74.7%    ZACN⁺ cells in Treg cells:

[NF-023] (μM)

MODULATORS OF ZINC ACTIVATED CATION CHANNEL

CROSS REFERENCE TO RELATED APPLICATIONS

This application is a National Phase of International Application No. PCT/US2017/013015, filed Jan. 11, 2017, which designated the U.S. and that International Application was published under PCT Article 21(2) in English. This application also includes a claim of priority under 35 U.S.C. § 119(e) to U.S. Provisional Application No. 62/277,422, filed Jan. 11, 2016, the entirety of which is hereby incorporated by reference.

STATEMENT REGARDING FEDERALLY SPONSORED RESEARCH OR DEVELOPMENT

This invention was made with made in part with government support under grant number GM085237 awarded by the National Institutes of Health and National Institute of General Medical Sciences. The Government has certain rights in the invention.

FIELD OF THE INVENTION

The present disclosure is in the field of ion channels and modulators thereof.

BACKGROUND OF THE DISCLOSURE

All publications herein are incorporated by reference to the same extent as if each individual publication or patent application was specifically and individually indicated to be incorporated by reference. The following description includes information that may be useful in understanding the present invention. It is not an admission that any of the information provided herein is prior art, or that any publication specifically or implicitly referenced is prior art.

Neurotransmitter-operated ion channels play important roles in fast synaptic transmission between neurons. They are also called ligand-gated ion channels. The Zinc-activated cation channel (ZACN) was discovered about a decade ago, and it was found to be expressed in several human brain regions, as well as in other tissues, such as lung, liver, and pancreas. ZACN protein is expressed in the neurons of human hippocampus. In recent years, more and more genomes have been sequenced. Despite this progress, the expression pattern of ZACN is not fully characterized, and its physiological function remains unclear.

SUMMARY OF THE DISCLOSURE

Various embodiments disclosed herein include methods of modulating the function of Zinc Activated Cation Channel (ZACN) in a subject comprising: administering to the subject a pharmaceutically effective dosage of ATP, a purinergic compound, red or blue dye, heparin or heparin analog, desipramine, reboxetine, and/or tomoxetine; and modulating the function of ZACN in the subject. In one embodiment, the purinergic compound is suramin. In one embodiment, the purinergic compound is one or more of NF-157, NF-279, NF-110, NF-023, and/or NF-449. In one embodiment, the heparin analog is pentosan polysulfate. In one embodiment, the red or blue dye is neutral red, toluidine blue, methylene blue, bromophenol blue, trypan blue, bromothymol blue, Evans blue, brilliant blue, and/or chicago sky blue. In one embodiment, the subject is a human. In one embodiment, modulating the function of ZACN regulates immune tolerance in the subject. In one embodiment, the subject is afflicted with an autoimmune disease. In one embodiment, modulating the function of ZACN provides a treatment to the autoimmune disease in the subject. In one embodiment, the subject is afflicted with an inflammatory disease. In one embodiment, modulating the function of ZACN regulates inflammation in the subject. In one embodiment, the subject has undergone or is about to undergo tissue or organ implantation. In one embodiment, modulating the function of ZACN regulates immune tolerance to the tissue or organ implantation in the subject. In one embodiment, the subject is afflicted with a cancer. In one embodiment, modulating the function of ZACN provides a treatment for the cancer in the subject. In one embodiment, the subject is prone to depression. In one embodiment, modulating the function of ZACN provides a treatment for depression in the subject. In one embodiment, modulating the function of ZACN provides a method of preventing depression in the subject.

Various embodiments disclosed herein also include methods of treating a disease in a subject comprising: administering to the subject a pharmaceutically effective dosage of a compound capable of modulating the function of the Zinc Activated Cation Channel (ZACN); and treating the disease. In one embodiment, the compound is ATP, a purinergic compound, red or blue dye, heparin or heparin analog, desipramine, reboxetine, and/or tomoxetine. In one embodiment, the purinergic compound is suramin. In one embodiment, the purinergic compound is one or more of NF-157, NF-279, NF-110, NF-023, and/or NF-449. In one embodiment, the heparin analog is pentosan polysulfate. In one embodiment, the red or blue dye is neutral red, toluidine blue, methylene blue, bromophenol blue, trypan blue, bromothymol blue, Evans blue, brilliant blue, and/or chicago sky blue. In one embodiment, the disease is an autoimmune disease, tissue implantation, organ implantation, depression, or cancer.

Various embodiments disclosed herein also include methods of diagnosing susceptibility to a disease in a subject, comprising: obtaining a sample from the subject; assaying the sample to determine the presence or absence of abnormal ZACN expression; and diagnosing susceptibility to the disease in the subject based on the presence of abnormal ZACN expression. In one embodiment, the disease is associated with regulatory T cells (Treg cells) expression. In one embodiment, Treg cells expression comprises inducement by IL-2 and/or TGF-beta 1. In one embodiment, the disease is an autoimmune disorder. In one embodiment, the disease is cancer. In one embodiment, the disease is an inflammatory disease. In one embodiment, abnormal ZACN expression includes abnormalities of Treg cells. In one embodiment, the disease is associated with biomarker FOXP3 expression. In one embodiment, the disease is malignant bone marrow-Myeloma, breast cancer, or malignant breast-invasive ductal carcinoma. In one embodiment, the disease is depression.

Other embodiments include a composition, comprising one or more Zinc Activated Cation Channel (ZACN) modulating compounds, and a pharmaceutically acceptable carrier. In another embodiment, the one or more ZACN modulating compounds comprises a pharmaceutically effective dosage of ATP, a purinergic compound, red or blue dye, heparin or heparin analog, desipramine, reboxetine, and/or tomoxetine, or a pharmaceutical equivalent, analog, derivative and/or salt thereof.

Other features and advantages of the invention will become apparent from the following detailed description, taken in conjunction with the accompanying drawings, which illustrate, by way of example, various embodiments of the invention.

DESCRIPTION OF THE DRAWINGS

Exemplary embodiments are illustrated in referenced figures. It is intended that the embodiments and figures disclosed herein are to be considered illustrative rather than restrictive.

DETAILED DESCRIPTION

Figure 1:
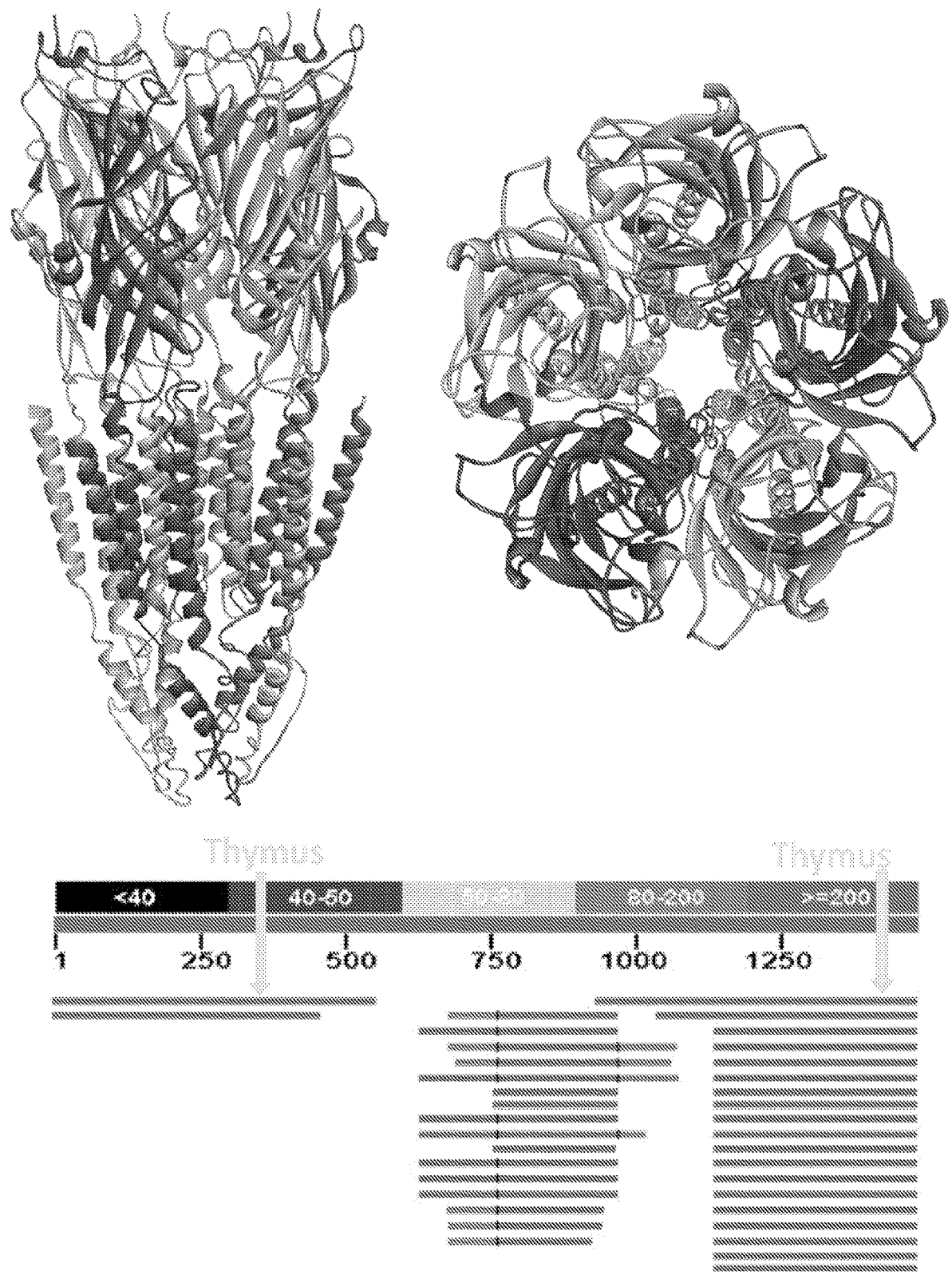
FIG. 1 illustrates, in accordance with the embodiments herein, that ZACN (with the homology model), a cation selective ion channel, is a member of the pentameric ligand-gated ion channel/receptor superfamily. Nicotinic receptors, 5-HT3 receptors, and ZACN receptors are examples of cation channel receptors; while $GABA_{A/C}$ receptors, glycine receptors, and other receptors (such as invertebrate and bacteria pLGIC) are examples of anion channel receptors. Since the ZACN gene is partially overlapped with the last exon of EXOC7 gene, but is in opposite orientation, ZACN mRNA sequence was used to BLAST search NCBI human EST (expressed sequence tag) database. This resulted in identification of 4 EST clones (out of 7 total hits) from human thymus, suggesting that the ZACN mRNA is expressed in the human thymus.

All references cited herein are incorporated by reference in their entirety as though they are fully set forth. Unless defined otherwise, technical and scientific terms used herein have the same meaning as commonly understood by one of ordinary skill in the art to which this invention belongs. Hornyak, et al., Introduction to Nanoscience and Nanotechnology, CRC Press (2008); Singleton et al., Dictionary of Microbiology and Molecular Biology 3rd ed., J. Wiley & Sons (New York, N.Y. 2001); March, Advanced Organic Chemistry Reactions, Mechanisms and Structure 7th ed., J. Wiley & Sons (New York, N.Y. 2013); and Sambrook and Russel, Molecular Cloning: A Laboratory Manual 4th ed., Cold Spring Harbor Laboratory Press (Cold Spring Harbor, N.Y. 2012), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

As used herein, the term "T reg" or "Treg" refers to regulatory T cells.

As used herein, the term "ZACN" refers to Zinc Activated Cation Channel.

As used herein, the term "control tissue" refers to either a tissue from a healthy individual or a healthy tissue from a patient. In some embodiments, the control tissue and the tissue being examined are matched in cell type.

In one embodiment, the present disclosure provides a method of modulating the function of Zinc Activated Cation Channel in a subject comprising administering to the subject a pharmaceutically effective dosage of heparin or heparin analog, ATP, a purinergic compound, suramin, red or blue dye, desipramine, reboxetine, and/or tomoxetine. In one embodiment, modulating the function of ZACN regulates immune tolerance in the subject. In one embodiment, the present disclosure provides a method of regulating immune tolerance in a subject by administering to the subject a pharmaceutically effective dosage of heparin or heparin analog, ATP, suramin, a purinergic compound, red or blue dye, d-tubocurarine, desipramine, reboxetine, and/or tomoxetine; and regulating immune tolerance by modulating the function of the Zinc Activated Cation Channel (ZACN). In one embodiment, the purinergic compound is one or more of suramin, NF-157, NF-279, NF-110, NF-023, and/or NF-449. In one embodiment, the heparin analog is pentosan polysulfate. In one embodiment, the red or blue dye is neutral red, toluidine blue, methylene blue, bromophenol blue, trypan blue, bromothymol blue, Evans blue, brilliant blue, and/or chicago sky blue. In one embodiment, the subject is a human. In one embodiment, the subject is afflicted with an autoimmune disease. In one embodiment, modulating the function of ZACN provides a treatment to the autoimmune disease in the subject. In one embodiment, the subject is afflicted with an inflammatory disease. In one embodiment, modulating the function of ZACN regulates inflammation in the subject. In one embodiment, the subject has undergone or is about to undergo tissue or organ implantation. In one embodiment, modulating the function of ZACN regulates and/or modulates immune tolerance to the tissue or organ implantation. In one embodiment, the subject is afflicted with cancer. In one embodiment, modulating the function of ZACN provides a treatment for the cancer in the subject. In one embodiment, the subject is afflicted with depression. In one embodiment, modulating the function of ZACN provides a treatment for depression in the subject. In one embodiment, modulating the function of ZACN provides a method for preventing depression in the subject.

In one embodiment, the present disclosure provides a method of treating a disease in a subject comprising administering to the subject a pharmaceutically effective dosage of a compound capable of modulating the function of the ZACN; and treating the disease. In one embodiment, the compound is heparin or heparin analog, ATP, a purinergic compound, suramin, red or blue dye, d-tubocurarine, desipramine, reboxetine, and/or tomoxetine. In one embodiment, the purinergic compound is one or more of suramin, NF-157, NF-279, NF-110, NF-023, and/or NF-449. In one embodiment, the heparin analog is pentosan polysulfate. In one embodiment, the red or blue dye is neutral red, toluidine blue, methylene blue, bromophenol blue, trypan blue, bromothymol blue, Evans blue, brilliant blue, and/or chicago sky blue. In one embodiment, the disease is an autoimmune disease, inflammatory disease, tissue implantation, organ implantation, depression, or cancer.

In one embodiment, the present disclosure provides a method of diagnosing susceptibility to a disease in a subject, comprising obtaining a sample from the subject; assaying the sample to determine to presence or absence of abnormal ZACN expression; and diagnosing susceptibility to the disease in the subject based on the presence of abnormal ZACN expression. In one embodiment, the disease is associated with regulatory T cells (Treg cells) expression. In one embodiment, Treg cells expression includes inducement by IL-2 and/or TGF-beta 1. In one embodiment, the disease is an autoimmune disorder. In one embodiment, the disease is cancer. In one embodiment, abnormal ZACN expression includes abnormalities of Treg cells. In one embodiment, the disease is associated with biomarker FOXP3 expression. In one embodiment, the disease is malignant bone marrow-Myeloma, breast cancer, or malignant breast-invasive ductal carcinoma.

In one embodiment, the present disclosure provides a method of treating a disease and/or condition in a subject, comprising providing a composition comprising one or more inhibitors of ZACN signaling; and administering a therapeutically effective dosage of the composition to the subject. In one embodiment, the disease and/or condition is cancer. In one embodiment, the disease and/or condition is an autoimmune disorder. In one embodiment, the composition comprises d-tubocurarine. In one embodiment, the disease and/or condition is associated with biomarker FOXP3 expression. In one embodiment, the disease and/or condition is malignant bone marrow-Myeloma, breast cancer, or malignant breast-invasive ductal carcinoma. In one embodiment, the composition comprises one or more antidepressants.

In one embodiment, the present disclosure provides a method of detecting the presence of Treg cells in a tissue of a subject, comprising taking a sample from said tissue of said subject, incubating the tissue sample with one or more antibodies, performing an assay to detect ZACN expression, and determining the presence or absence of Treg cells based on the presence or absence of ZACN. In one embodiment, the present disclosure provides a method of diagnosing cancer and autoimmune diseases comprising comparing the expression level of ZACN in a tissue of a patient with that of a control tissue, wherein the presence of an increased expression level of ZACN in the tissue of the patient indicates the presence of cancer or an autoimmune disease. In one embodiment, the present disclosure provides a method of regulating immune tolerance, the method comprising modulating the function of ZACN by activating the ZACN channel to increase intracellular calcium in Treg cells; increased intracellular calcium in Treg cells activates the Treg cells; and activated Treg cells regulate immune tolerance. In one embodiment, the present disclosure provides a method of treating organ transplantation rejection, comprising modulating Treg function via modulation of ZACN activity and/or expression. In one embodiment, the present disclosure provides a method of treatment for depression comprising administering to a patient in need thereof, a pharmaceutically effective amount of an antidepressant medicine and $ZnCl_2$. In one embodiment, the present disclosure provides a method of preventing depression in an individual comprising modulating the expression of ZACN. In one embodiment, the present disclosure provides a method of diagnosing depression in an individual comprising detecting the effect of antidepressants on ZACN.

In various embodiments, the present invention provides pharmaceutical compositions including a pharmaceutically acceptable excipient along with a therapeutically effective amount of one or more Zinc Activated Cation Channel (ZACN) modulating compounds, for example. Or for example, a pharmaceutically effective dosage of ATP, a purinergic compound, red or blue dye, heparin or heparin analog, desipramine, reboxetine, and/or tomoxetine, or a pharmaceutical equivalent, analog, derivative and/or salt thereof. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal or parenteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins Pa., USA) (2000).

Typical dosages of an effective ZACN modulating compound, for example, can be in the ranges recommended by the manufacturer where known therapeutic compounds are used, and also as indicated to the skilled artisan by the in vitro responses or responses in animal models. Such dosages typically can be reduced by up to about one order of magnitude in concentration or amount without losing the relevant biological activity. Thus, the actual dosage will depend upon the judgment of the physician, the condition of the patient, and the effectiveness of the therapeutic method based, for example, on the in vitro responsiveness of the relevant primary cultured cells or histocultured tissue sample, such as biopsied malignant tumors, or the responses observed in the appropriate animal models, as previously described.

The present invention is also directed to a kit to modulate ZACN, for example. The kit is an assemblage of materials or components, including at least one of the inventive compositions. Thus, in some embodiments the kit contains a composition including one or more ZACN modulating compounds, as described above.

The exact nature of the components configured in the inventive kit depends on its intended purpose. For example, some embodiments are configured for the purpose of treating an immunological disorder or disease. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well known methods, preferably to provide a sterile, contaminant-free environment. As used herein, the term "package" refers to a suitable solid matrix or material such as glass, plastic, paper, foil, and the like, capable of holding the individual kit components. Thus, for example, a package can be a glass vial used to contain suitable quantities of an inventive composition containing one or more ZACN modulating compounds. The packaging material generally has an external label which indicates the contents and/or purpose of the kit and/or its components.

Embodiments of the present disclosure are further described in the following examples. The examples are merely illustrative and do not in any way limit the scope of the invention as claimed.

EXAMPLES

Example 1

Generally

Neurotransmitter-operated ion channels play important roles in fast synaptic transmission between neurons. They are also called ligand-gated ion channels. The pentameric ligand-gated ion channel superfamily in vertebrate animals is also termed the cys-loop receptors. Traditionally, the cys-loop receptor family includes cationic selective nicotinic acetylcholine receptors, serotonin receptors type 3, anionic selective $GABA_{A/C}$ receptors, and glycine receptors. Over a decade ago, a novel class of the cys-loop receptors were identified through BLAST database searching and molecular cloning from the human fetal brain and spinal cord cDNA library. When exogenously expressed in HEK cells, this novel channel exhibited spontaneous activity. The spontaneous activity was blocked by d-tubocurarine, but not by other ligand-gated ion channel antagonists. However, it did not respond to any known neurotransmitters. Zinc activated this receptor dose-dependently. The reversal potential of the zinc-activated current was close to zero and could be shifted by changing intracellular potassium concentration. Thus, the novel channel was named as zinc-activated cation channel (ZACN).

ZACN mRNA is expressed in several human brain regions, as well as in other tissues, such as lung, liver, pancreas. ZACN protein, the homology model of which is illustrated in FIG. 1, is expressed in the neurons of human hippocampus. In recent years, more and more genomes have been sequenced. To date, the NCBI database has listed 164 ZACN genes, mostly predicted, in mammals, including some rodents, suggesting that it is an evolutionarily new gene with potential novel physiological functions. However, ZACN gene does not exist in rat and mouse. Despite this progress, the expression pattern of ZACN is not fully characterized, and its physiological function remains unclear.

Example 2

Materials

The following normal human paraffin fixed tissue slide were purchased:
  Fetal thymus (Abcam, Cambridge, Mass., USA; Amsbio, Cambridge, Mass., USA),
  Adult thymus (Novus Biologicals Inc, Littleton, Colo., USA; US BiomaxInc, Rockville, Md., USA),
  Fetal spleen (Abcam),
  Adult spleen (Abcam, US BiomaxInc),
  Adult Lymph node (US BiomaxInc),
  Adult Lymph node (US BiomaxInc),
  Adult Tonsil (US BiomaxInc),
  Adult Appendix (US BiomaxInc),
  Adult Bone Marrow (US BiomaxInc).

Human peripheral blood mononuclear cells were purchased from HemaCareCorp. (Van Nuys, Calif., USA).

The following antibodies were used for Immunohistochemistry:
  CD4 (MT-310) mouse monoclonal antibody (Santa Cruz Biotechnology Inc., Dallas, Tex., USA),
  CD25/IL-2R alpha chain (IL2R.1) mouse monoclonal antibody (MAS-12680) (Pierce Biotechnology, Rockford, Ill., USA),
  FOXP3 [236A/E7] mouse monoclonal antibody (Abcam),
  Anti-ZACN-EC (extracellular epitope: 157-170aa) rabbit-anti-human polyclonal antibody (AZC-001) (Alomone, Jerusalem, Israel.),
  Anti-ZACN-IC (intracellular epitope: 340-370aa) rabbit-anti-human polyclonal antibody (LS-C160709) (LsBio, Seattle, Wash., USA).

For detection the following secondary antibodies were used for immunohistochemistry: Goat anti-mouse IgGAlexa Fluor 488 (Molecular Probes, Eugene, Oreg., USA), and Goat anti-rabbit IgGAlexa Fluor 546 (Molecular Probes).

Fluoroshield mounting medium with DAPI was purchased from Abcam. All other chemicals were purchased from Sigma-Aldrich (St. Louis, Mo., USA).

Example 3

Fluorescent Immunostaining Analysis of ZACN Expression in Thymus and in Peripheral Immune Organs (Spleen, Tonsil, and Lymph Nodes)

Paraffin-embedded human lymphatic tissue slides and tissue arrays were purchased from multiple vendors (such as, Abcam (thymus), Amsbio (thymus, spleen), US Biomax (lymphatic tissue arrays), Novus Biologicals (thymus)). These were de-paraffinized in xylene, and the tissue section was rehydrated. The antigen was retrieved by heating the tissue in sodium citrate buffer (10 mM sodium citrate, 0.05% Tween-20, pH=6.0) at 98° C. for 20 min. The slides were cooled and rinsed with de-ionized water for 10 min and then washed twice with TBS containing 0.025% Triton-X (TBS-T) to permeabilize the cell membrane.

Tissue slides were serum blocked with 10% BSA-TBS for 2 hours at room temperature, prior to their dual incubation with the appropriate primary antibodies (anti-CD4, 1:100; anti-CD25, 1:100; or anti-FOXP3, 1:100; and anti-ZACN (intracellular), 1:50; or anti-ZACN (extracellular), 1:100; all diluted in 1% BSA-TBS) for 1 hour at room temperature. The slides were washed three times with TBS-T, before their incubation in 1:200 dilution in 1% BSA-TBS of secondary antibodies: goat anti-mouse IgGAlexa Fluor 488 and goat anti-rabbit IgGAlexa Fluor 546 (Molecular Probes, Eugene, Oreg., USA) at room temperature for 1 h and protected from ambient light. Slides were then washed twice with TBS and once with de-ionized $H_2O$, and fluoroshield mounting medium with DAPI (4',6 diamidino-2-phenylindole) was applied. Tissue slides were imaged by a Carl Zeiss LSM-710 laser scanning confocal microscope (Carl Zeiss, Oberkochen, Germany).

Figure 2:
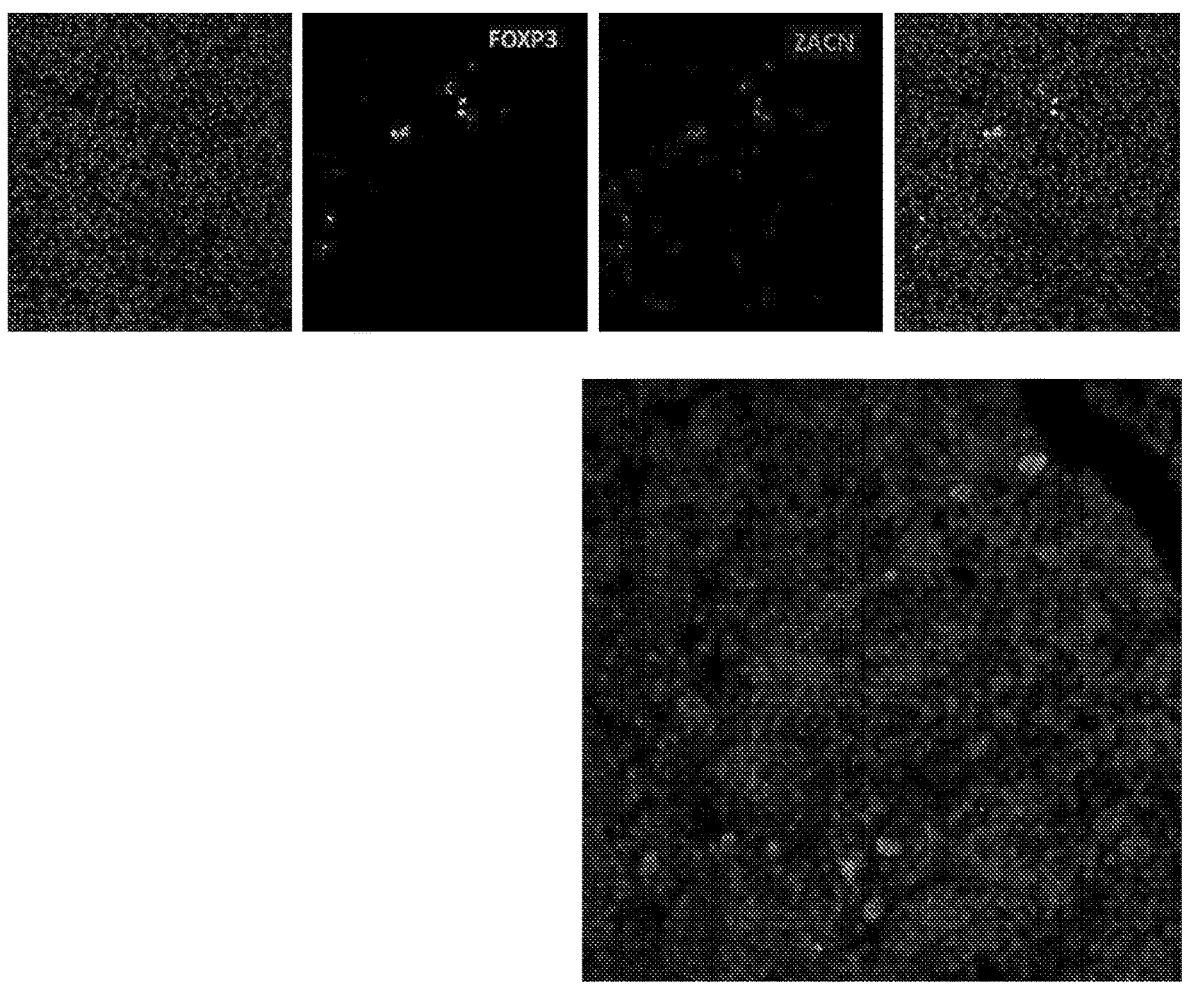
FIG. 2 illustrates, in accordance with the embodiments herein, ZACN immunostaining in human thymus with FOXP3. ZACN protein expression, identified by immunostaining, is localized in a small fraction of thymus cells, and overlaps with Treg specific marker FOXP3.

A. ZACN Protein was Expressed in Treg Cells in the Human Thymus:

cDNA clones of ZACN found in NCBI human EST database suggested that ZACN is expressed in human thymus cells. To further characterize the expression pattern of ZACN in the human thymus, immunostaining of the human thymus slides with anti-ZACN-IC antibody was performed. In one illustrative embodiment, a small fraction of the human thymus cells were ZACN+. This revealed that ZACN+ cells were a small subset of T cells present in the thymus. To further identify the cell type of the ZACN+ cells, human thymus tissues were co-immunostained with anti-CD4 and anti-ZACN-IC antibodies. In one embodiment, ZACN+ cells were a subset of CD4+ cells, illustrating that they were CD4+ T cells. Co-staining of thymus with anti-ZACN-IC with anti-FOXP3 antibodies revealed that ZACN immunostaining nearly completely overlapped with FOXP3 immunostaining (FIG. 2, FIG. 3), suggesting that ZACN is expressed in regulatory T cells. Similarly, another relative Treg specific marker, CD25, gave similar results. Therefore, these results show that ZACN protein was specifically expressed in the Treg cells in the human thymus.

The possibility of false staining of ZACN antibody to some unknown protein was eliminated as follows: anti-ZACN-EC antibody, as a sample, was tested with anti-FOXP3 antibody for co-immunostaining of the human PBMC. In one embodiment, the ZACN-EC+ cells were also FOXP3+. Thus, the overlapping of immunostaining for FOXP3 separately with those by two antibodies against completely different domains of ZACN eliminates the possibility of false positive staining of ZACN antibody to some unknown protein. Moreover, this validates the finding that ZACN protein was expressed in Treg cells in the human thymus.

B. ZACN Protein was Expressed in Treg Cells in Human Peripheral Lymph Organs and PBMC.

Figure 3:
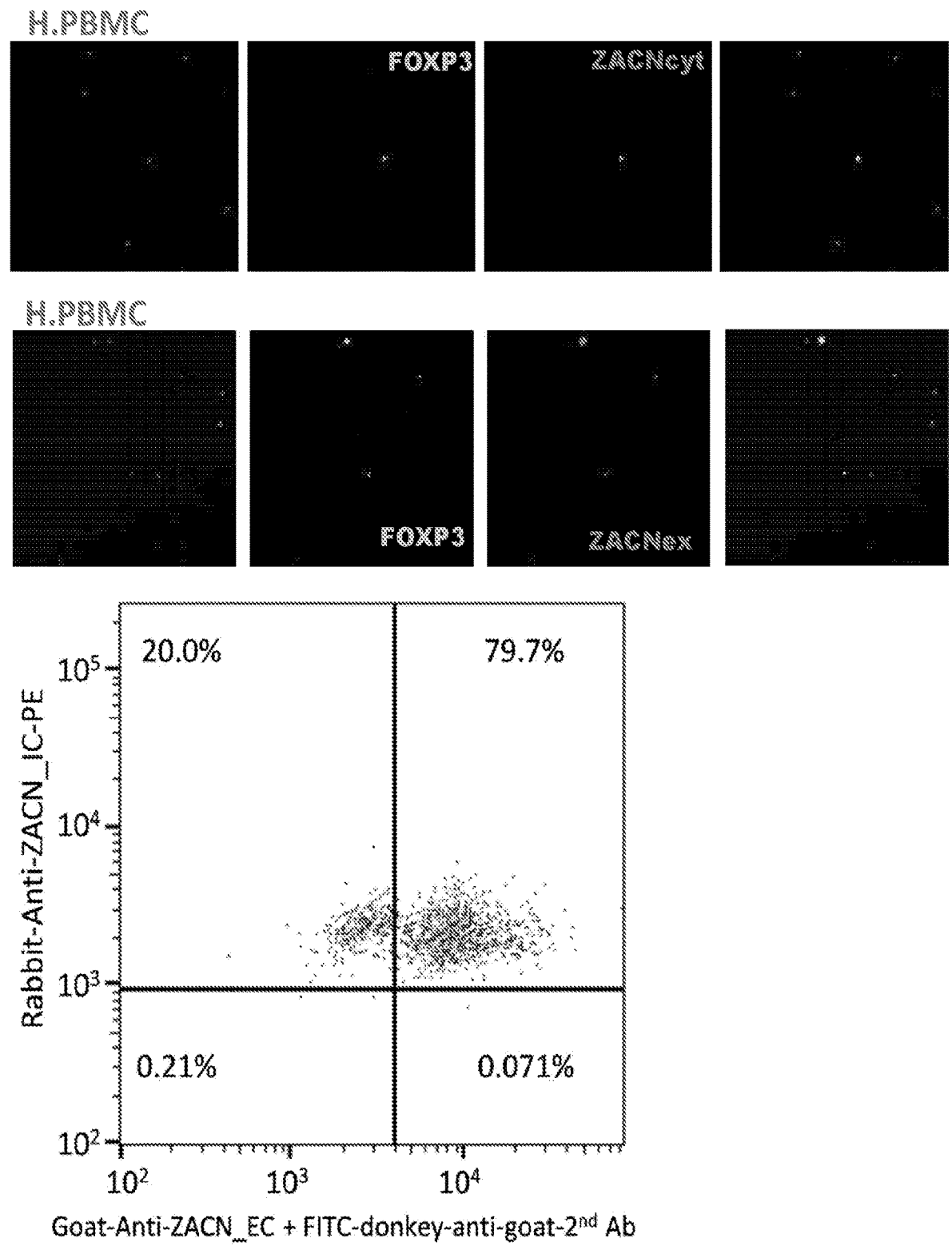
FIG. 3 illustrates, in accordance with the embodiments herein, human ZACN antibody validation. The figure illustrates the immunostaining with both anti-ZACN antibodies against intracellular or extracellular epitopes of ZACN overlap with Treg cell specific marker: FOXP3. ZACN protein was expressed in some human peripheral blood mononuclear cells (PBMCs) with FOXP3. Detection of ZACN by both antibodies (against intracellular vs. extracellular epitopes) resulted in similar coexpression detection with FOXP3, suggesting that the detection is specific for ZACN, and not non-specific cross-reactions. FACS analysis of two ZACN antibodies also showed that they both can recognize the major CD4+CD25+ T cell population in human PBMCs.
Figure 4:
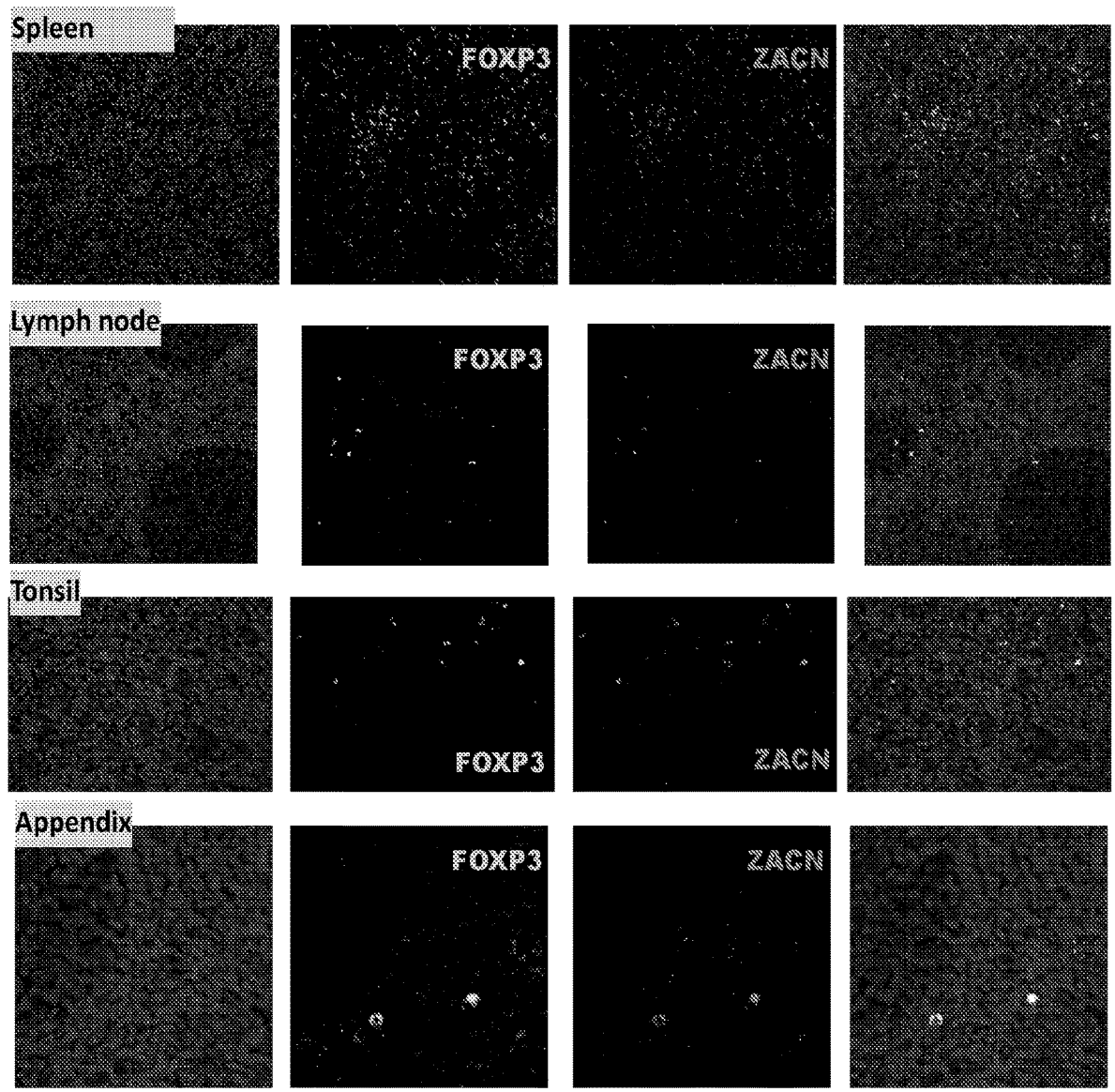
FIG. 4 illustrates, in accordance with the embodiments herein, ZACN protein expression in other lymph organs overlapping with FOXP3 by immunostaining.

Natural Treg cells are not only in the thymus, but also exist in peripheral lymph organs and PBMCs. In one embodiment, as illustrated in FIG. 3, ZACN was expressed in the Treg cells in the peripheral lymph organs. Furthermore, a Gene Expression Omnibus (GEO) profile identified that ZACN mRNA was also expressed in other lymph organs. To confirm this at the protein level and with cell specificity, the inventors performed co-immunostaining of ZACN along with other T cell markers. ZACN+ staining highly overlapped with FOXP3+ staining at the cellular level in the spleen, lymph nodes, tonsil, and PBMCs, as shown in FIG. 4. These results further illustrated that ZACN protein is expressed in natural Treg cells in the immune system.

Figure 5:
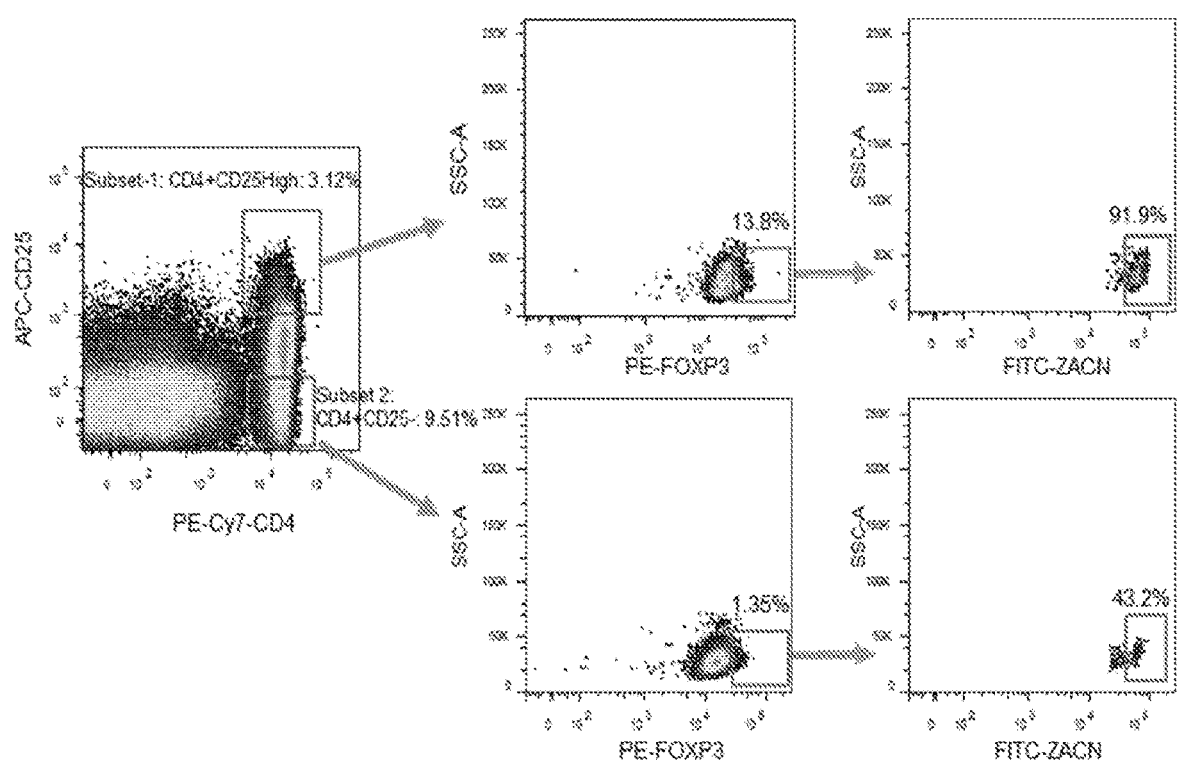
FIG. 5 illustrates, in accordance with the embodiments herein, that the FACS (Fluorescence activated cell sorting) analysis of human peripheral blood mononuclear cells (PBMC) reveals that ZACN is expressed (stained by ZACN antibody against intracellular epitope) in the majority of CD4+CD25+FOXP3+ cells, suggesting that ZACN is expressed in naturally occurring Treg cells.

C. FACS Analysis of PBMCs:

FACS analysis, illustrated in FIGS. 3 and 5, provided a quantitative analysis of the overlapping of immunostainings of ZACN protein and other T cell markers. Fresh human PBMCs were used in the FACS analysis. ZACN+ cells are a small subset of CD4+CD25− cells, and a larger subset of CD4+CD25+ cells. Approximately 92% overlap was found between ZACN and FOXP3 immunostaining in CD4+ CD25+FOXP3+ cells. In contrast, CD8+ cells did not overlap with ZACN+ cells. These results were consistent with prior findings that natural regulatory T (nTreg) cells specifically express ZACN in the immune system.

Example 4

ZACN Expression in Peripheral Blood T Cells (for Antibody Validation)

Human frozen peripheral blood mononuclear cells (PBMC) were purchased from VWR International, and Astarte Biologics. The cells were suspended in RPMI 1640 media (Gibco Life Technologies, Grand Island, N.Y., USA) containing 5% FBS, 2 mM L-glutamine, 0.5 mM sodium pyruvate, and 100 U/μg/ml penicillin/streptomycin and incubated at 37° C. in a humidified atmosphere of 95% air/5% CO2 for 16 hours prior to immunostaining. Cells were fixed with methanol at −20° C. for 10 min, washed three times with Tris buffered saline (TBS), re-suspended in de-ionized $H_2O$ and then fixed to Superfrost Plus Microscope Slides (Fisher Scientific, Pittsburgh, Pa., USA). The PBMC affixed slides were then treated to the same procedures as the de-paraffinized tissue slides for immunohistochemistry.

Example 5

Induction of ZACN Expression in iTreg Cells

Figure 6:
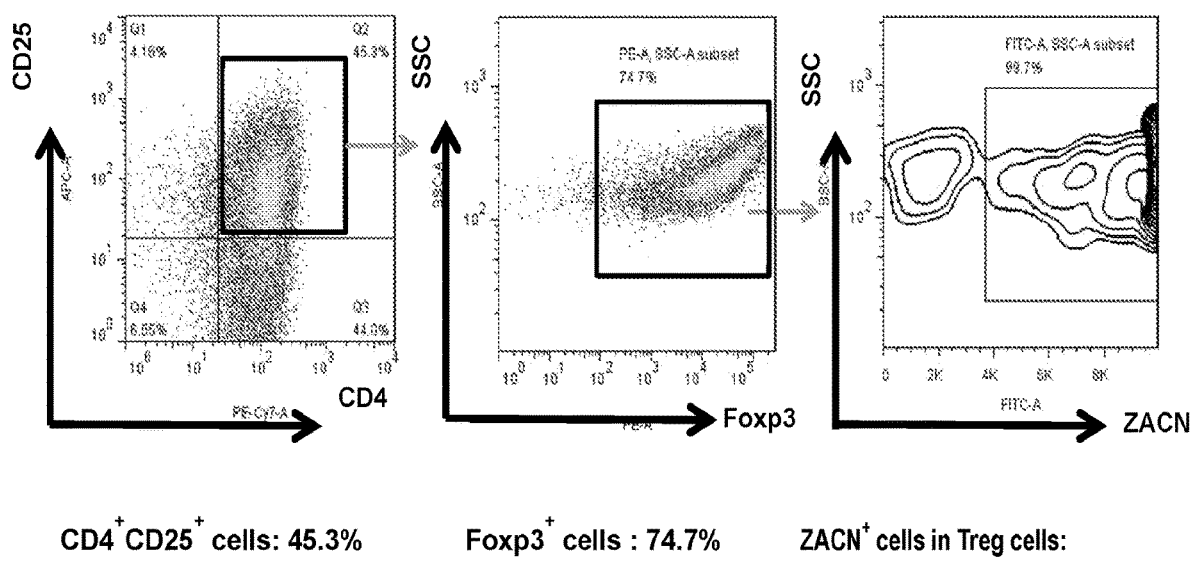
FIG. 6 illustrates, in accordance with the embodiments herein, that the induction of Treg cells by IL-2 and TGF-b1 in vitro also induces expression of ZACN in Treg cells by FACS analysis.

Induction of induced Treg cells (iTreg) by TGF-β1 and IL-2 also induces expression of FOXP3. Since ZACN expression in T cells is highly correlated to FOXP3 expression, it is likely that induction of iTreg also induces ZACN expression in these cells. To test this possibility, the inventors induced iTreg from the naïve-T cells isolated from fresh human PBMCs. Untouched CD4+ naïve-T cells were isolated from the fresh human PBMCs by negative selection using EasySep Human Naïve CD4+ T Cell Enrichment Kit (Stemcell Technologies, Vancouver, Canada). As illustrated in FIG. 6, FACS analysis revealed that the iTreg also expressed ZACN protein. After induction by TGF-β1 and IL-2 for 6 days, nearly three quarters of CD4+/CD25+ cells were FOXP3+. ZACN immunostaining almost completely (99.75%) overlapped with FOXP3 staining. Thus, ZACN expression in CD4+ cells can be induced by TGF-β1 and IL-2 in parallel with FOXP3 expression. This induction pattern illustrates that ZACN has an important function in Treg cells.

Example 6

Calcium Influx Assay

Treg cells were loaded with calcium sensitive fluorescent dye X-Rhod-1 AM (cell permeant) (2 µM) for 60 min at room temperature. After wash, the cells were placed onto a glass-bottom petri dish with coated glass surface to allow cells attached to the glass surface. The fluorescence was detected using a microscope-based detection system with a different filter set (excitation filter ET560/40x, T585LPxr dichroic mirror, and ET630/75m emission filter). The fluorescence signal, first in the absence and then in the presence of a ZACN agonist, was low-pass filtered with a signal filter at 1 Hz and digitized with a Digidata1440 digitizer at 10 Hz.

Example 7

Patch-Clamp Studies

Live Treg cells (CD4+CD25$^{high}$) were obtained by FACS for patch-clamp study using whole cell patch-clamp configuration using Axon GeneClamp500B with a patch-clamp headstage (electrode 3). A piezo translator-controlled theta (e) tubing is used for rapid solution exchange for drug application (zinc or other agonists, or antagonists).

Example 8

In Vitro CFSE-Based Treg Suppression Assay

Live Treg cells (CD4+CD25$^{high}$) and conventional T cells (Tconv cells) (CD4+CD25−) are obtained by immunomagnetic cell isolation kit from human iTreg. Tconv cells are labeled with CFSE (10 uM for 10 min). After washing, the labeled cells are distributed into multiple wells (1×10$^5$/well) in a round bottom 96-well plate with various numbers (2-fold serial dilutions from 1×10$^5$/well) of Treg cells in each well. The mixed cells (Treg and Tconv with different ratios) are co-cultured for 72 h in the presence of anti-CD3/CD28-coated sulfate latex beads. The intensity of CFSE fluorescence that declines upon division of the labeled cells is measured by flow cytometry.

Example 9

ZACN is a Novel Target of Purinergic Agonists and Antagonists

Figure 9:
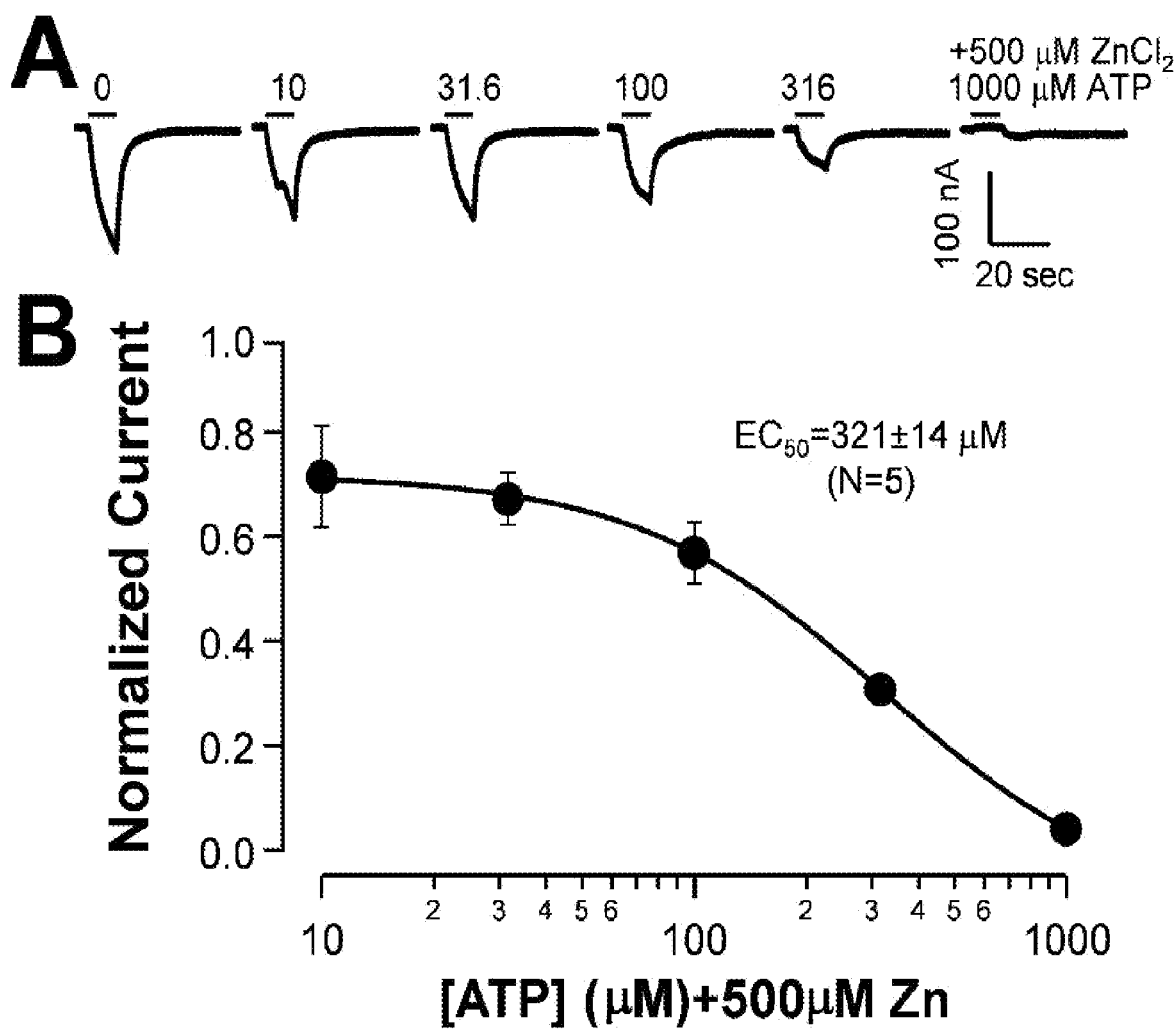
FIG. 9. illustrates, in accordance with the embodiments herein, that the extracellular ATP (ATP applied extracellularly) is an endogenous inhibitor of human ZACN. The extracellular ATP is released from intracellular compartment with cell injury. It is a purinergic agonist, and is considered a Danger signal that cause inflammation through activating purinergic P2Xs (ATP-gated cation channels) and P2Y (G-protein linked receptors) receptors. In one embodiment, ZACN is demonstrated to be a novel target of the endogenous purinergic agonist, acting as an antagonist on human ZACN. Thus, this channel would be related to the extracellular ATP-induced inflammation.

As further disclosed herein and illustrated for example in FIG. 9, the inventors have found that ZACN is a novel target of purinergic agonists and antagonists. Specifically, the P2X receptor agonist ATP is an antagonist of zinc induced current on ZACN, whereas many P2X antagonists, such as suramin, Evans blue, Trypan blue, NF157, NF-279, NF-110, NF-023, and NF-449, are agonists for ZACN. The inventors have also found that ATP is a positive allosteric modulator of suramin-induced current on ZACN.

Extracellular ATP can serve as an immune transmitter in the immune synapse between antigen presenting cell and T cell. Extracellular ATP released from injured cells is also a danger signal to initiate immune response and inflammation. Currently known extracellular ATP receptors are P2X (ion channels) and P2Y (G-protein-linked receptors) receptors. Extracellular ATP induces inflammation through these receptors, especially P2X7 receptor, which is a major target for new anti-inflammatory drug development. In one embodiment, the present disclosure provides a novel way of ATP action through ZACN functional regulation. In another embodiment, the present disclosure provides a novel drug target to develop new therapeutic drug to treat autoimmune diseases, inflammation, transplantation rejection, and cancer therapy. Since ZACN shares many ligands with P2X receptors, the present disclosure also suggests that it will be necessary to test ZACN sensitivity of any new drug development for P2X receptors.

In one embodiment, the current finding that ZACN as a novel target of purinergic agonist and antagonists would provide a novel mechanism to regulate immune function and inflammation by endogenous extracellular ATP. As is known to a skilled artisan, rats and mice do not have the ZACN gene. Thus the current results on ZACN would solve the mystery of the major discrepancy between mouse and human inflammation response—that is, why some successful mouse studies of inflammation fails in human clinical trials. One possibility is that, as this study revealed, ZACN share many ligands with P2X receptors. Thus, the newly developed drugs may antagonize P2X7 receptor AND activate ZACN at the same time, and endogenous ATP can potentiate the activation of a P2X antagonist on ZACN. This effect cannot be seen in animals without the ZACN gene.

In one embodiment, the present disclosure provides experimental evidence to show that extracellular ATP can modulate ZACN function in a complex way, depending on the agonist used for ZACN activation. It provides a novel way to understand immune regulation and inflammation through extracellular ATP.

In various embodiments, the present disclosure describes agonists, antagonists, positive and negative allosteric modulators for ZACN. In one embodiment, these compounds would be a new generation of anti-inflammatory drugs, or could be used for the treatment of autoimmune diseases, transplantation rejection, and cancer.

Example 10

Nitro Blue Tetrazolium is a Selective Agonist for the Zinc Activated Cation Channel To date the only known agonist and antagonist for ZACN are Zn$^{2+}$ (agonist) and d-tubocurarine (antagonist). These two compounds have multiple targets. Thus, to better understand the novel ZACN receptor, more selective agonist(s) or antagonist(s) were identified. The *Xenopus laevis* oocytes expression system and two-electrode voltage-clamp was used to determine that Nitro Blue Tetrazolium (NBT) was a new agonist for ZACN. Unlike Zn$^{2+}$, whose EC$_{50}$ on ZACN expressed in *X. laevis* oocytes was 1.66 mM, NBT acted on ZACN at a much lower concentration with an EC$_{50}$ at 17.04

μM. In addition, application of NBT to other members of the Cys-loop receptors, including $GABA_A$ (α1β2γ2 & α6β2δ), $GABA_C$ (ρ1), serotonin (5HT3A), glycine (α1), nACh (α4β2 and α7) receptors, elicited no response. Together, this data illustrated that NBT was a selective agonist for ZACN. This is the most potent ZACN agonist (with the lowest EC50) as disclosed herein.

Example 11

Other Blue Dyes and a Red Dye as Novel Agonists/Antagonists of Human ZACN

The inventors have further found that four other blue dyes that do not belong purinergic antagonists, can also activate the human ZACN. These blue dyes are bromophenol blue, bromothymol blue, brilliant blue, and Chicago sky blue. The inventors also found that three structurally related dyes, neutral red, toluidine blue, and methylene blue, are human ZACN antagonists. They all have two sensitivities. The high sensitivity component is in nano-molar range, and the low sensitivity form is in micromolar range. One noticeable dye is methylene blue, which is a FDA approved injection drug for drug induced methemoglobinemia. It also has anti-inflammatory effect, and it has been used in clinical trials in treating Alzheimer's patients.

Example 12

Heparin and Heparin Analog are Agonists of ZACN

As disclosed herein, the inventors have found that ZACN is expressed in the human regulatory T cells. The inventors have further found that heparin and a heparin analog are agonists for ZACN. As readily known to one skilled in the art, heparin is produced, stored, and released by mast cells. Treg cells can activate mast cells to mediate regional immune suppression. Heparin released from activated mast cells could represent a positive feedback to enhance immune tolerance. Thus, current disclosure provides a novel mechanism to regulate immune tolerance.

The current disclosure also provides a new opportunity for drug discovery to modulate immune tolerance by blocking or enhancing heparin effect on ZACN. In one embodiment, the inventors have found that a semi-synthetic heparin analog, pentosan polysulfate (with 15-fold reduced anticoagulant activity), is also a novel agonist of the human ZACN with high efficacy. Pentosan polysulfate is a clinically prescribed drug with a brand name Elmiron, which has been used to treat bladder inflammation. The present disclosure suggests that heparin and its analogs, such as pentosan polysulfate, could be used in the treatment of autoimmune diseases and tissue and organ transplantation. The present disclosure also provides a novel mechanism to regulate immune tolerance through the interactions between the Treg cells and mast cell, while providing new opportunities for drug discovery for immune tolerance, treating autoimmune diseases and transplantation rejection.

While the inventors have shown that heparin and its analogs are novel endogenous agonists for ZACN, many heparin analogs may also have anticoagulant activity. Thus, in one embodiment, the drug development for heparin enhancing or antagonizing drugs would need to minimize their anticoagulant activity. In one embodiment, these new drug molecules would be positive and negative allosteric modulators for heparin activation of ZACN. These drug molecules would bind to a ZACN site that is different from the binding site for heparin, and positively or negatively modulate heparin effect.

Example 13

Novel Agonists and Antagonists of ZACN

Figure 7:
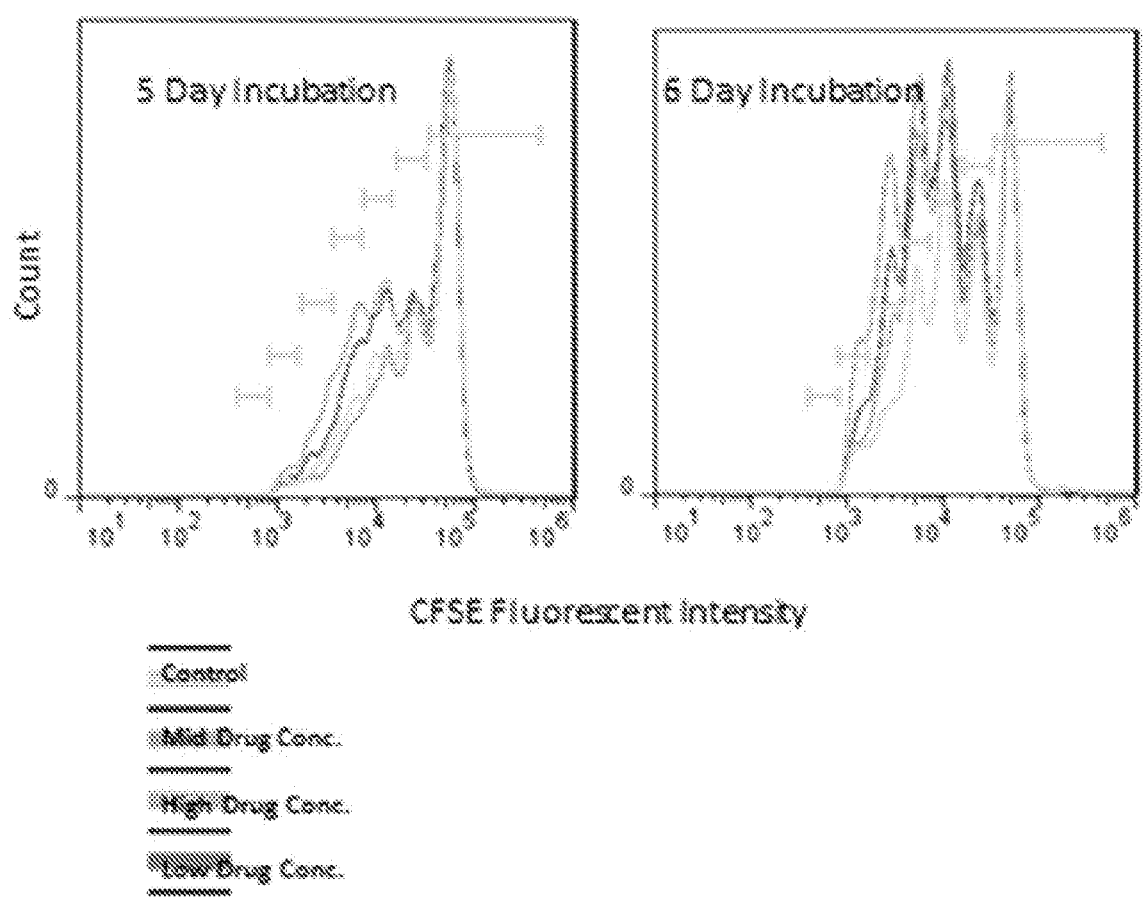
FIG. 7 illustrates, in accordance with the embodiments herein, the influence of Zinc/d-tubocurarine on iTreg suppression function. CFSE Immunosuppression Assay uses a cell permeable reactive fluorescent dye, CFSE. After entering cells, CFSE interacts with intracellular proteins, and permanently stain the cell. The fluorescence intensity will decrease along with the T cell division. Results demonstrated that high concentration of zinc (1 mM) killed T cells. The ZACN antagonist, d-tubocurarine, inhibited the iTreg-induced immunosuppression of T cell division, suggesting that ZACN is important for iTreg function.

As disclosed throughout the disclosure, and specifically in FIG. 7, Zinc and/or d-tubocurarine has an influence on iTreg suppression function. CFSE Immunosuppression Assay uses a cell permeable reactive fluorescent dye, CFSE. After entering cells, CFSE interacts with intracellular proteins, and permanently stain the cell. The fluorescence intensity will decrease along with the T cell division. Results demonstrated that high concentration of zinc (1 mM) killed T cells. The ZACN antagonist, d-tubocurarine, inhibited the iTreg-induced immunosuppression of T cell division, suggesting that ZACN is important for iTreg function.

Figure 8:
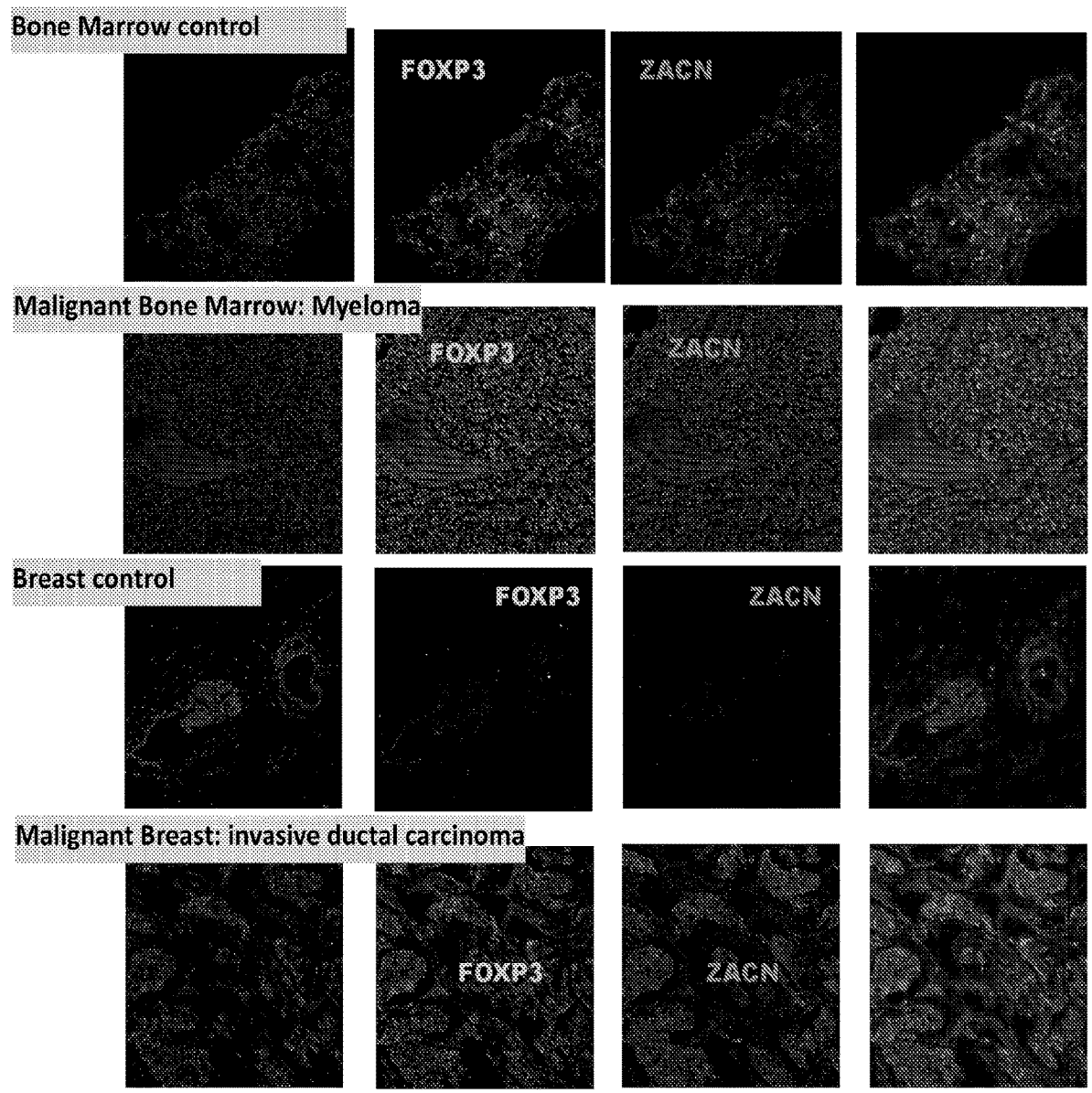
FIG. 8 illustrates, in accordance with the embodiments herein, the ZACN expression in human cancer tissues along with FOXP3: Bone marrow control, malignant bone marrow-Myeloma, breast control, malignant breast-invasive ductal carcinoma. The ZACN protein showed higher expression in malignant tissues than in control tissues.

As disclosed in FIG. 8, the ZACN expression in human cancer tissues along with FOXP3: Bone marrow control, malignant bone marrow-Myeloma, breast control, malignant breast-invasive ductal carcinoma are shown. The ZACN protein showed higher expression in malignant tissues than in control tissues.

FIGS. 10-21 illustrate experimental results on a few novel ZACN agonists disclosed herein. In one embodiment, these studies have been done in control oocytes without activation effect on the oocyte endogenous ion channels.

Figure 10:
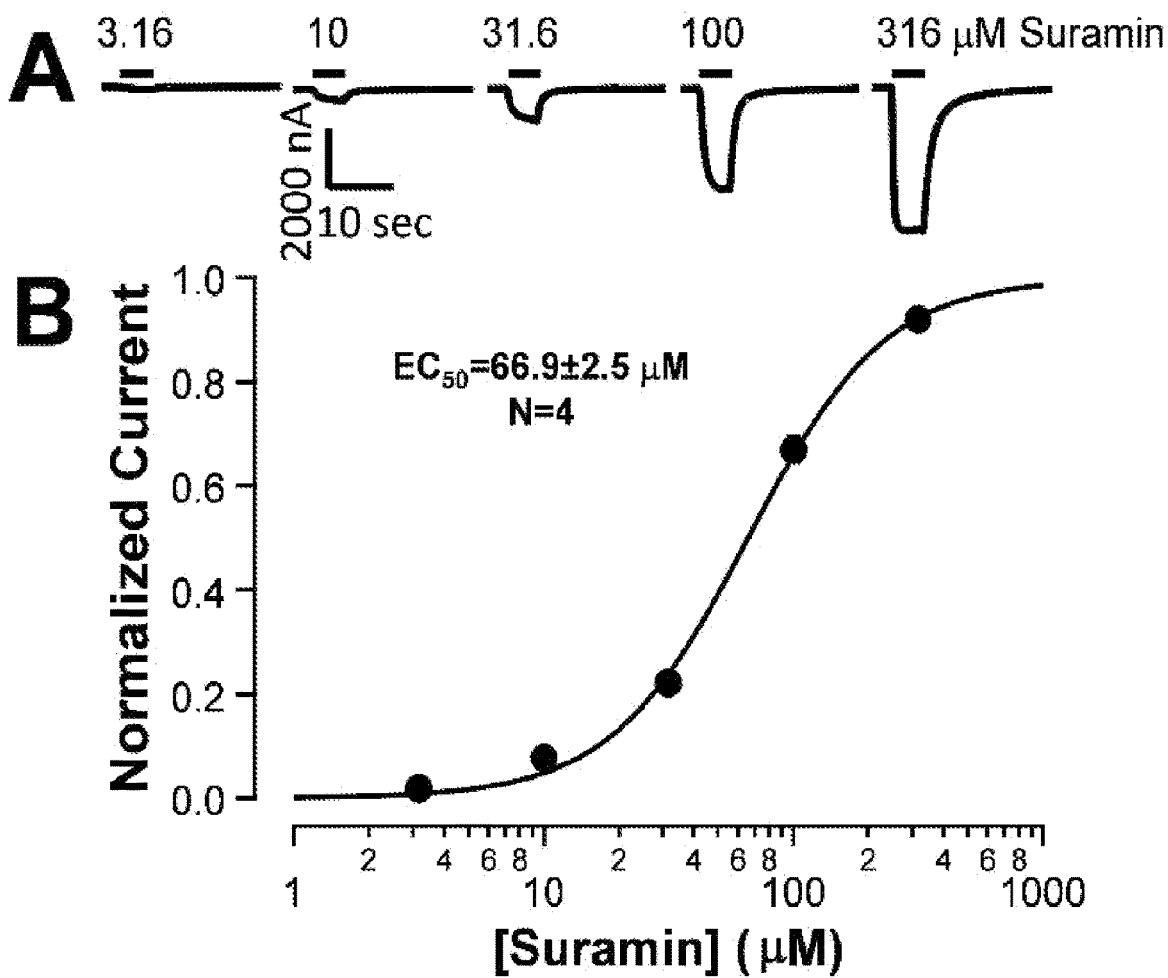
FIG. 10 illustrates, in accordance with the embodiments herein, the purinergic P2X antagonist, suramin, is an efficacious agonist to activate the human ZACN. Suramin, is also used clinically as an antiparasitic drug to treat sleeping sickness and onchocerciasis.
Figure 11:
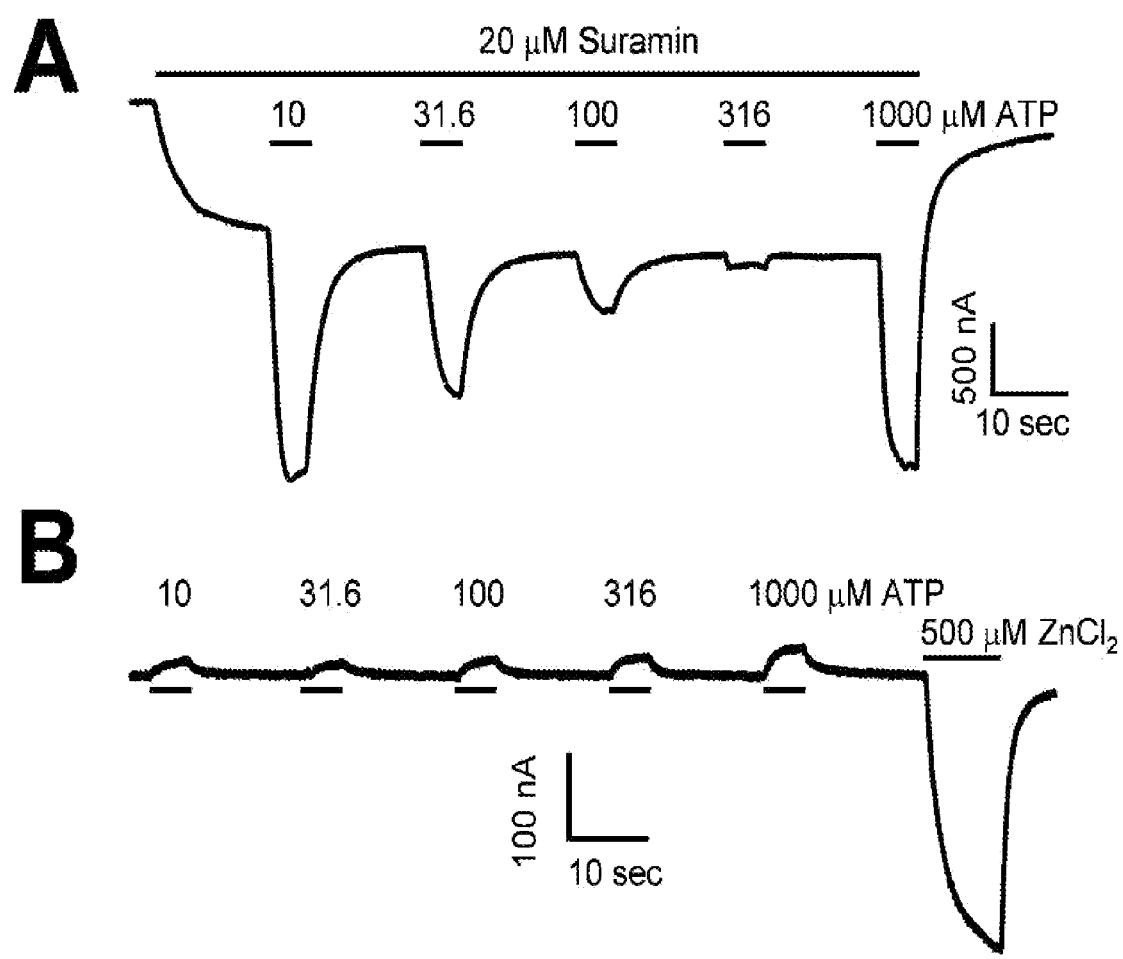
FIG. 11 illustrates, in accordance with the embodiments herein, the dual effect of ATP on human ZACN. As illustrated, the purinergic P2X agonist, ATP, can facilitate the channel opening by the purinergic P2X antagonist suramin, but only inhibit the spontaneously opening by itself, for the human ZACN. The dual effect of ATP on human ZACN inhibits spontaneous current and zinc-activated current, but potentiates suramin-activated current. This is a novel phenomenon that a purinergic agonist and an antagonist can synergistically activate human ZACN.

FIG. 10 illustrates the purinergic P2X antagonist, suramin, is an efficacious agonist to activate the human ZACN. Suramin is also used clinically as an antiparasitic drug to treat sleeping sickness and onchocerciasis. FIG. 11 illustrates the dual effect of ATP on human ZACN. As illustrated, the purinergic P2X agonist, ATP, can facilitate the channel opening by the purinergic P2X antagonist suramin, but only inhibit the spontaneously opening by itself, for the human ZACN. The dual effect of ATP on human ZACN inhibits spontaneous current and zinc-activated current, but potentiates suramin-activated current. This is a novel phenomenon that a purinergic agonist and an antagonist can synergistically activate human ZACN.

Figure 12:
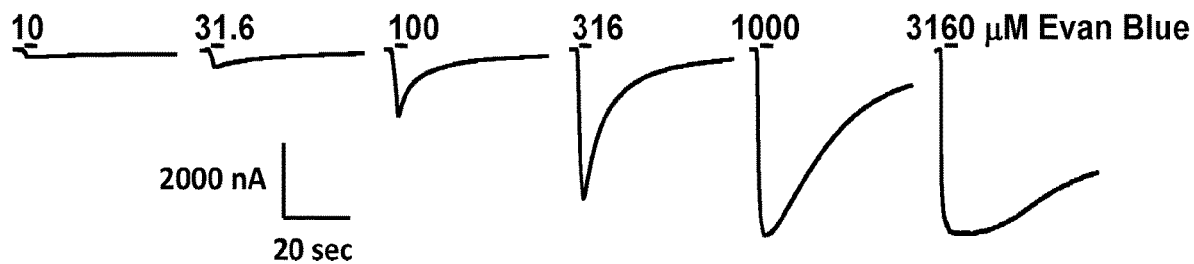
FIG. 12 illustrates, in accordance with the embodiments herein, the purinergic P2X antagonist, Evans blue, is an efficacious agonist to activate the human ZACN.
Figure 12:
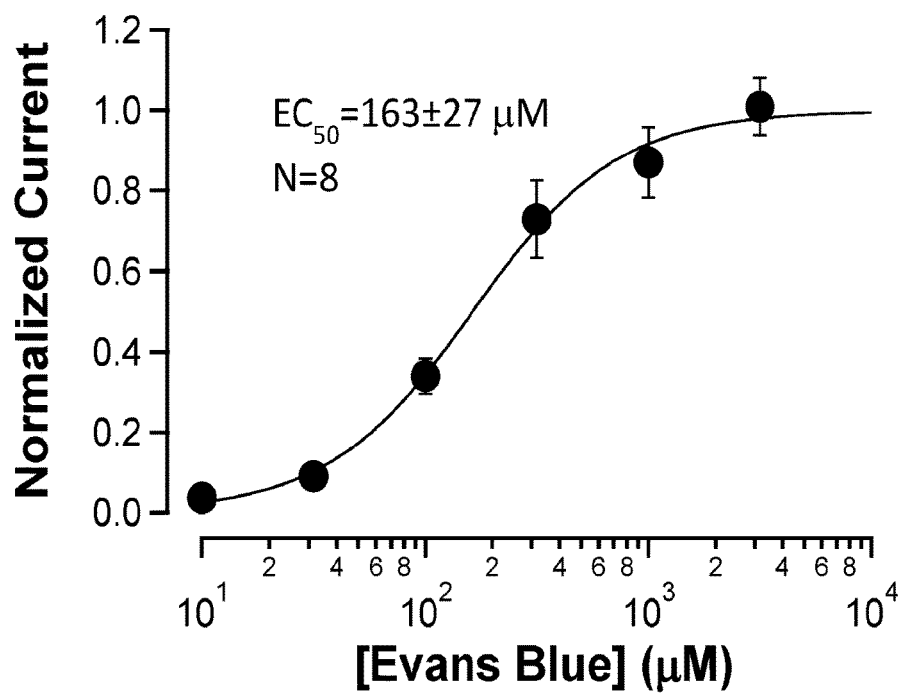
Figure 13:
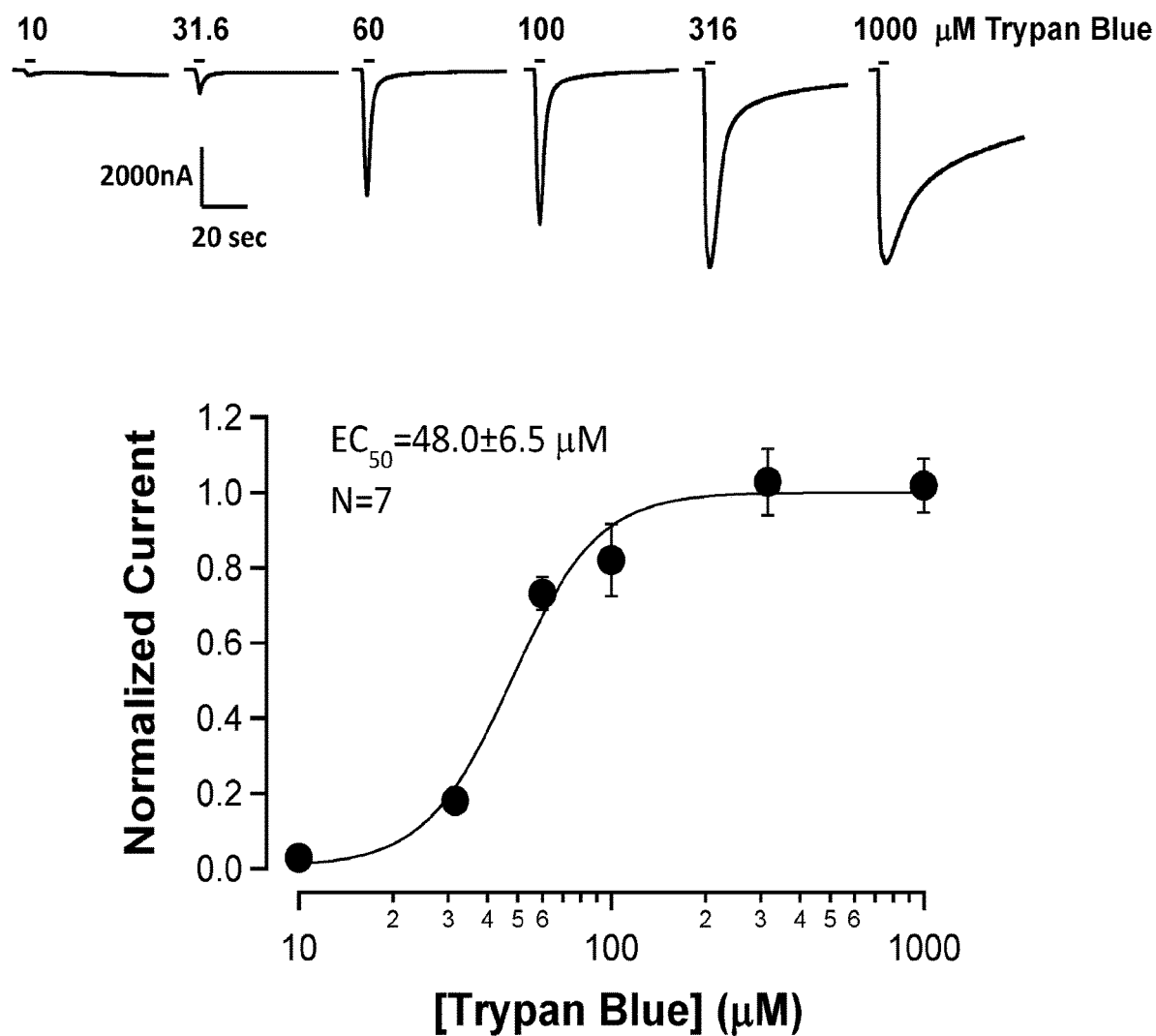
FIG. 13 illustrates, in accordance with the embodiments herein, the purinergic P2X antagonist, Trypan blue, is an efficacious agonist to activate the human ZACN.
Figure 14:
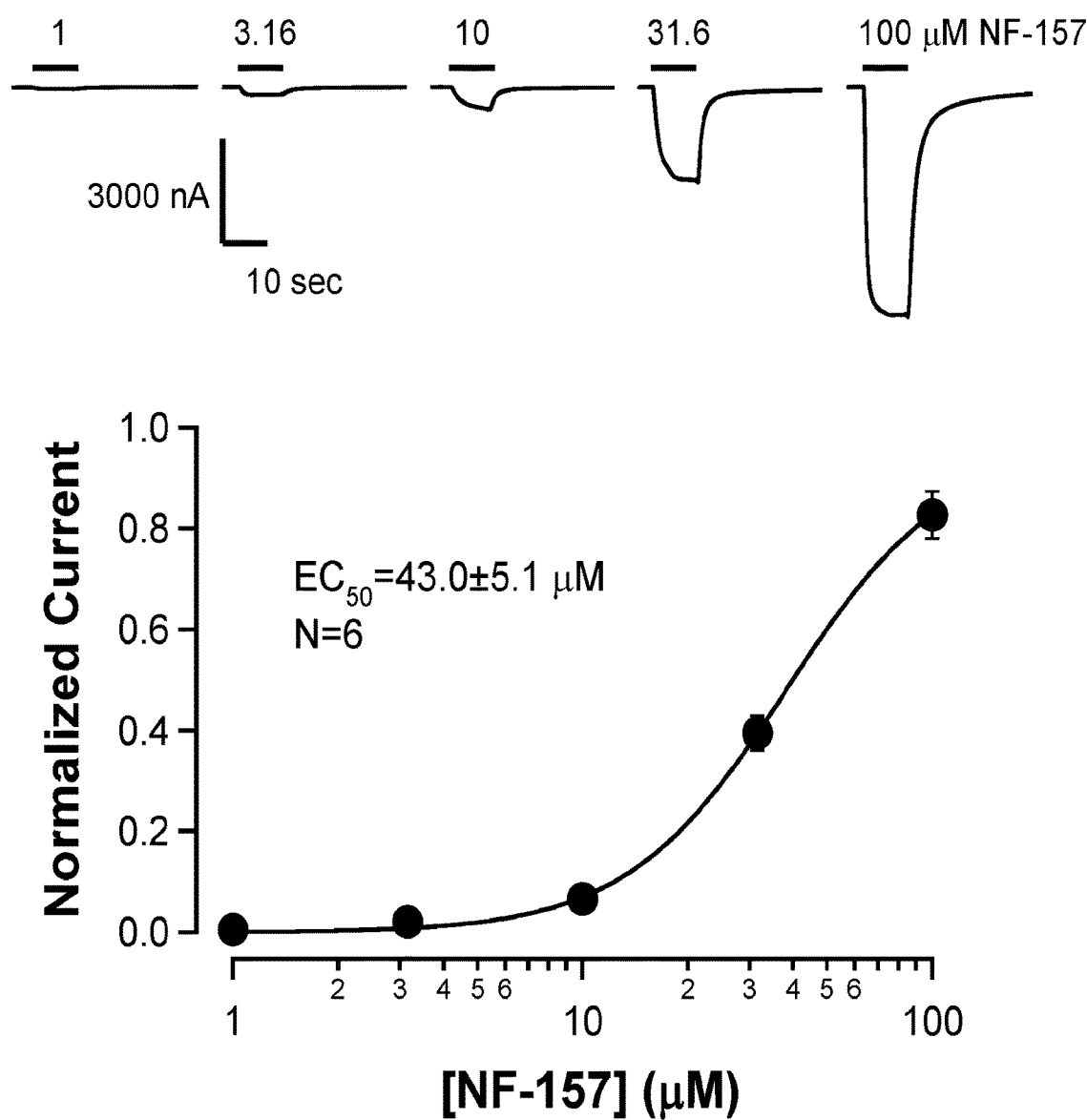
FIG. 14 illustrates, in accordance with the embodiments herein, the purinergic P2X antagonist, NF-157, is an efficacious agonist to activate the human ZACN.
Figure 15:
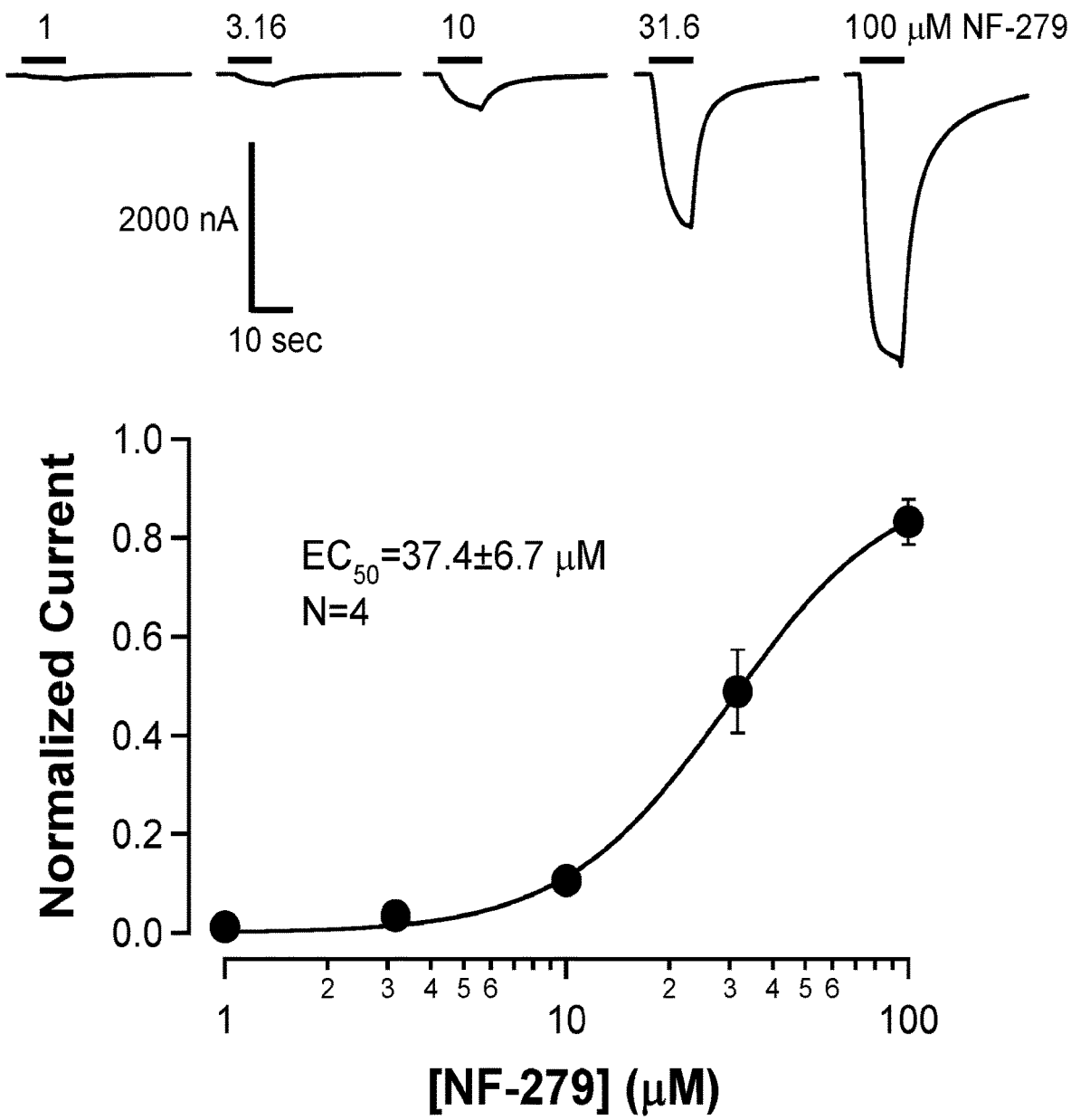
FIG. 15 illustrates, in accordance with the embodiments herein, the purinergic P2X antagonist, NF-279, is an efficacious agonist to activate the human ZACN.
Figure 16:
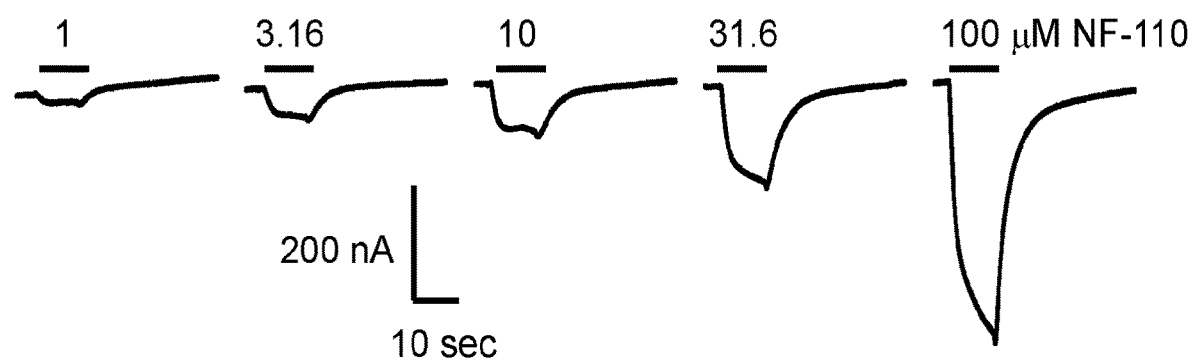
FIG. 16 illustrates, in accordance with the embodiments herein, the purinergic P2X antagonist, NF-110, is an agonist to activate the human ZACN.
Figure 16:
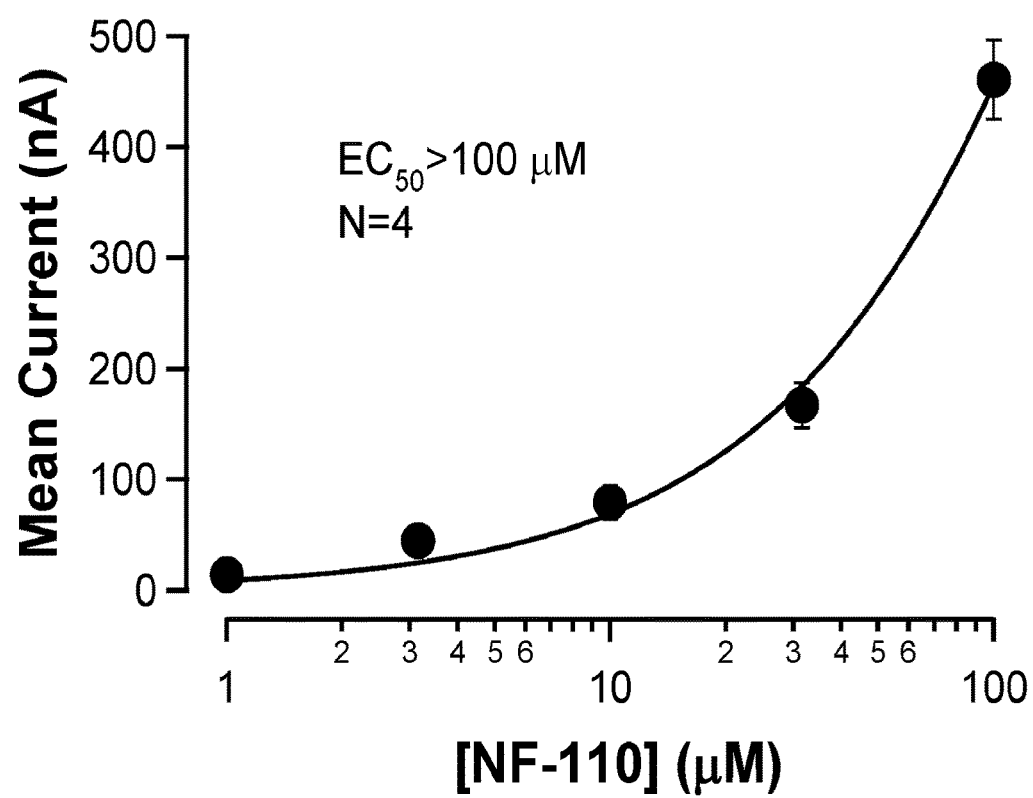
Figure 17:
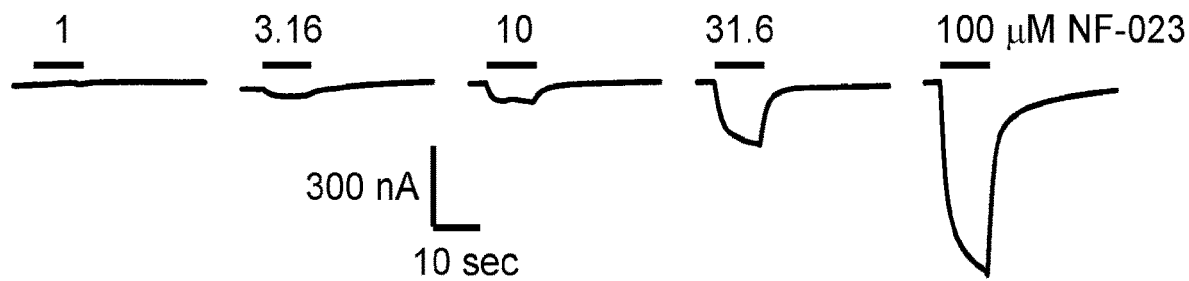
FIG. 17 illustrates, in accordance with the embodiments herein, the purinergic P2X antagonist, NF-023, is an agonist to activate the human ZACN.
Figure 17:
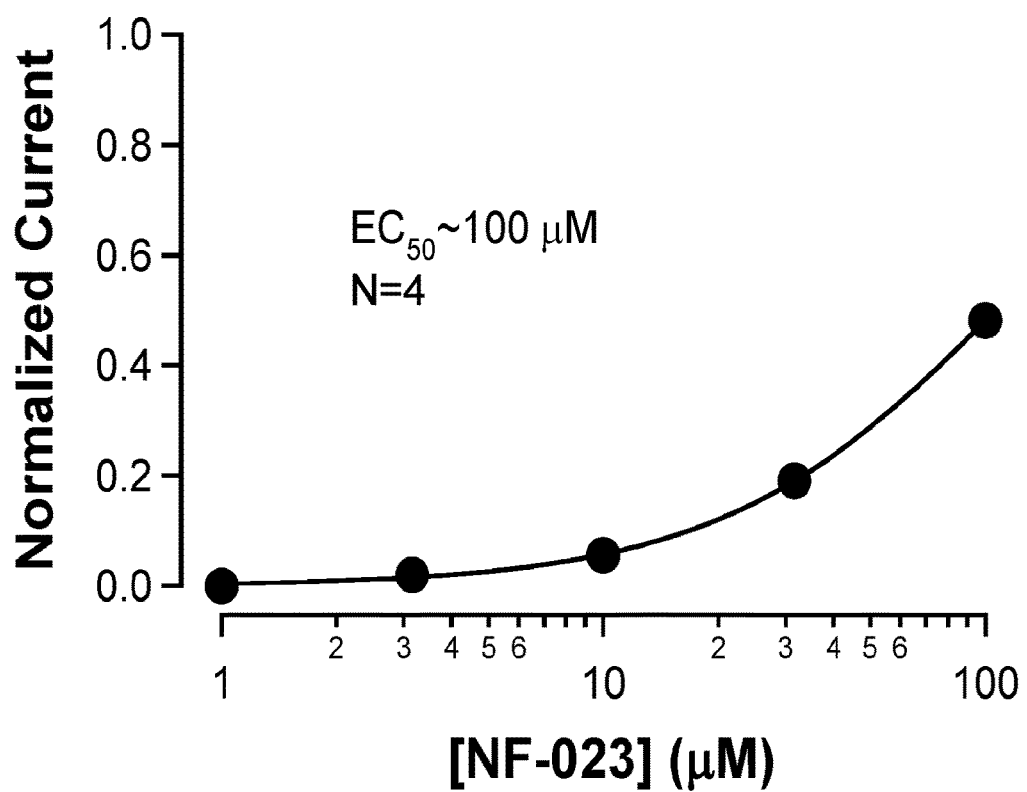
Figure 18:
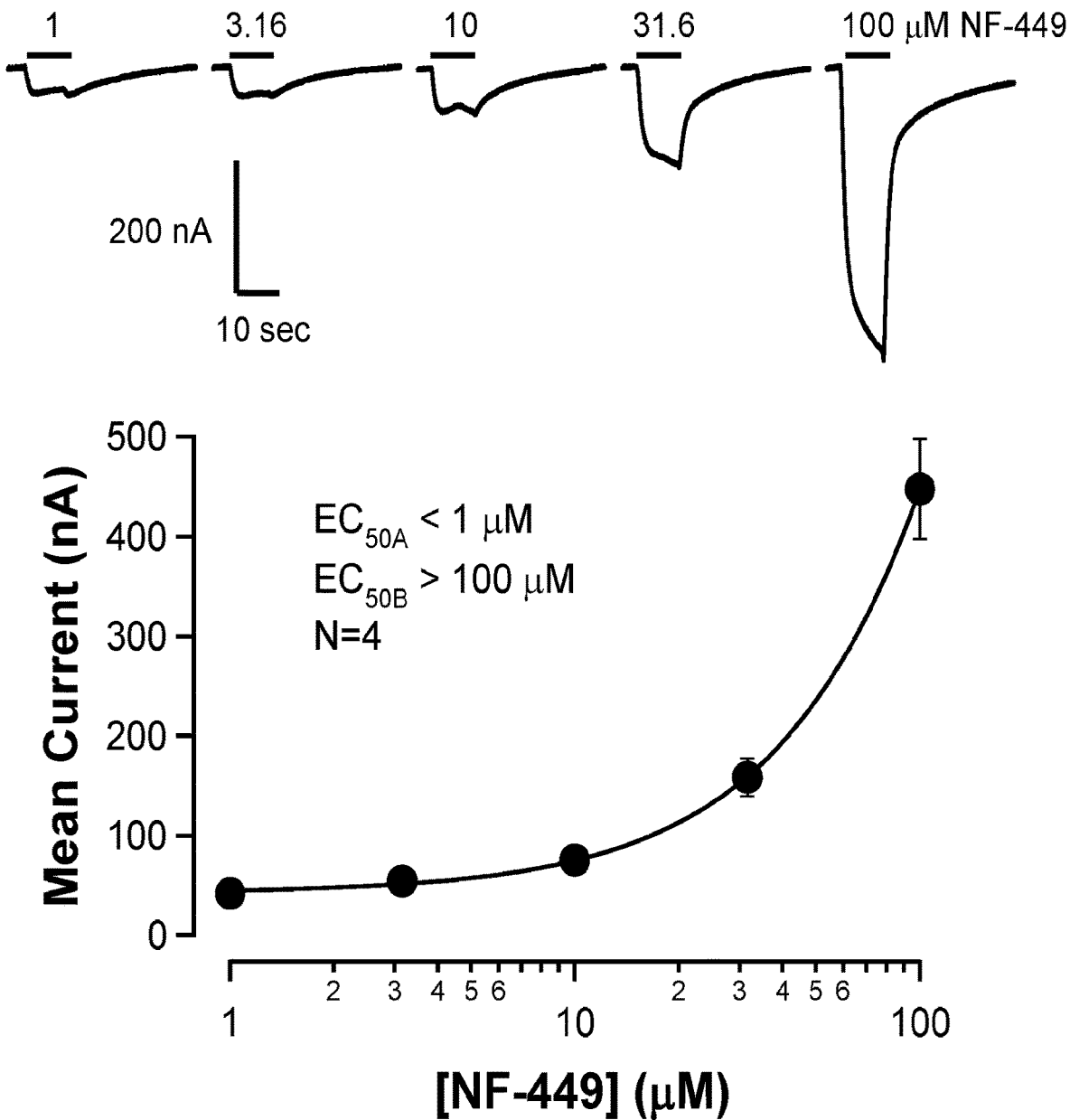
FIG. 18 illustrates, in accordance with the embodiments herein, the purinergic P2X antagonist, NF-449, is an agonist to activate the human ZACN. It has a small high sensitivity component, saturated at 1 µM.
Figure 19:
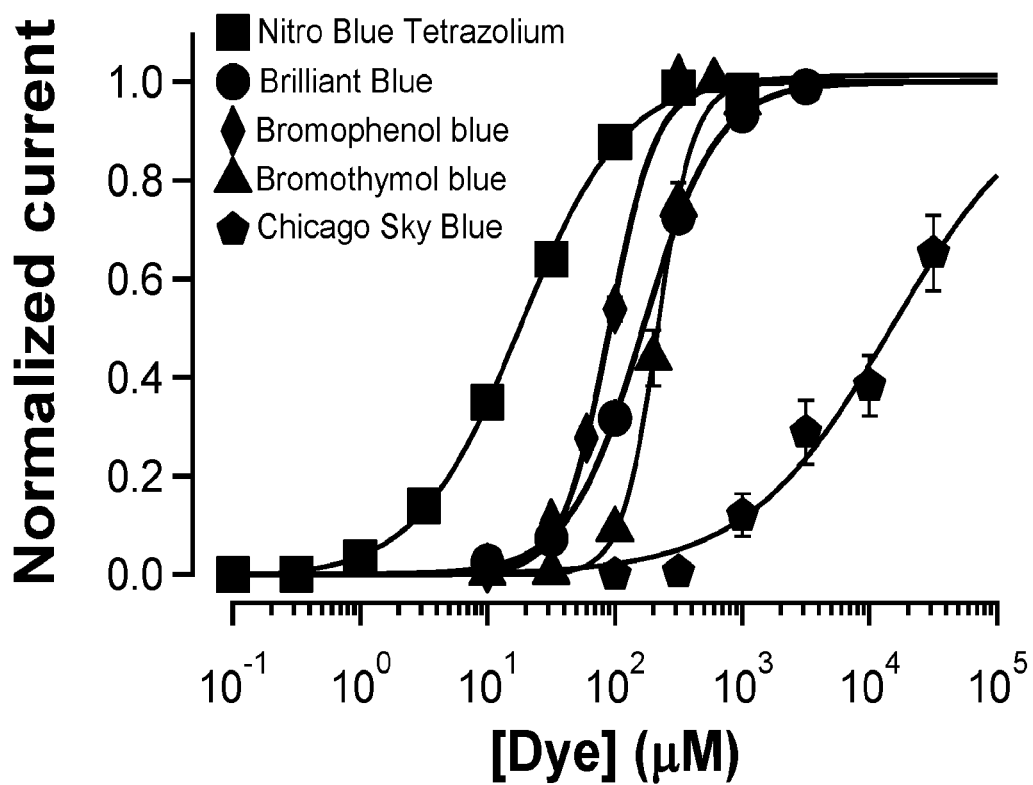
FIG. 19 illustrates, in accordance with the embodiments herein, five other blue dyes are agonists of the human ZACN with various potencies. Among them, nitro blue tetrazolium has the highest potency with an $EC_{50}$ of 17 µM.
Figure 20:
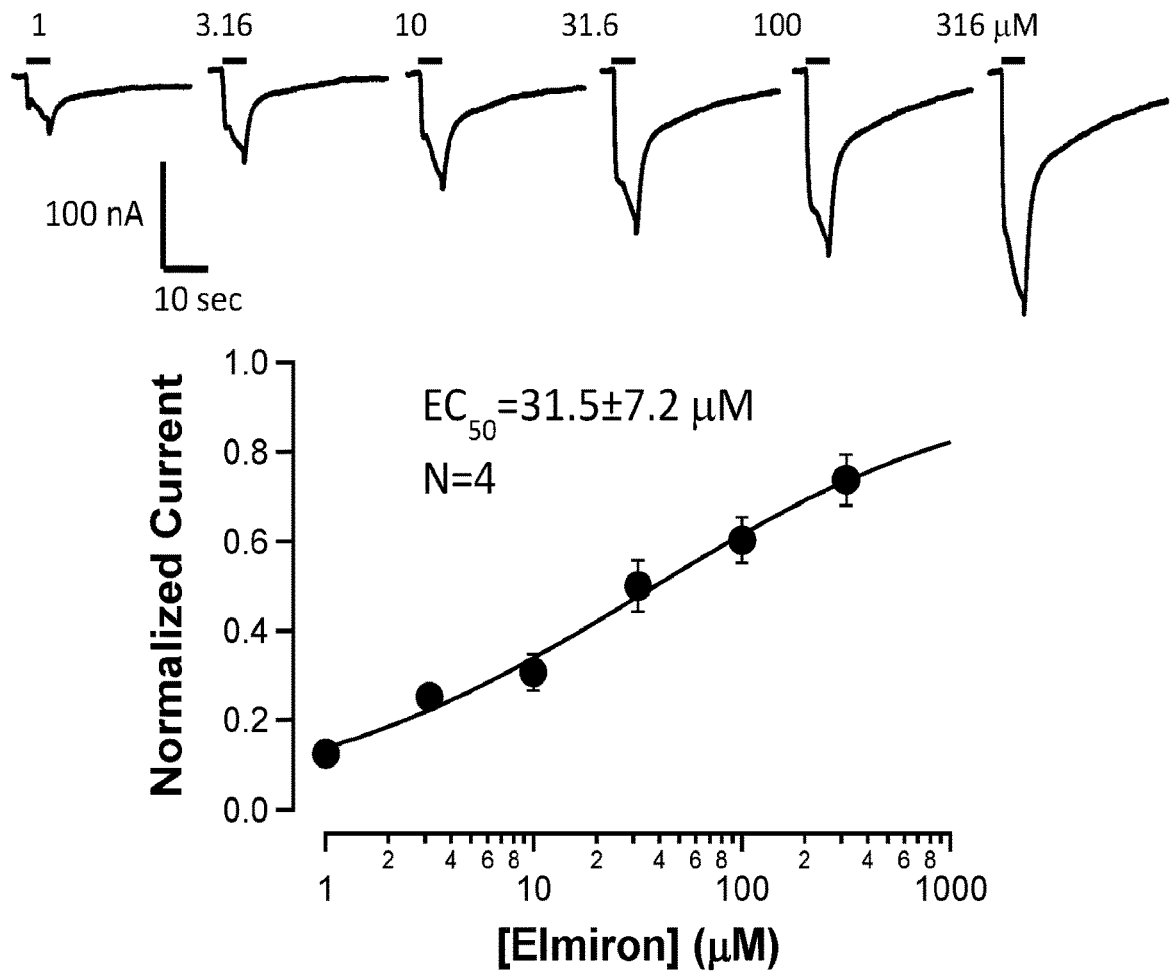
FIG. 20 illustrates, in accordance with the embodiments herein, heparin analog, pentosane polysulfate is an agonist of the human ZACN. The sodium salt of pentosan polysulfate was used; the compound was plant derived, with little anticoagulant activity, anti-inflammatory, orally active. The pentosan polysulfate was also anti-inflammatory, antiadhesive, and antimetastatic.
Figure 20:
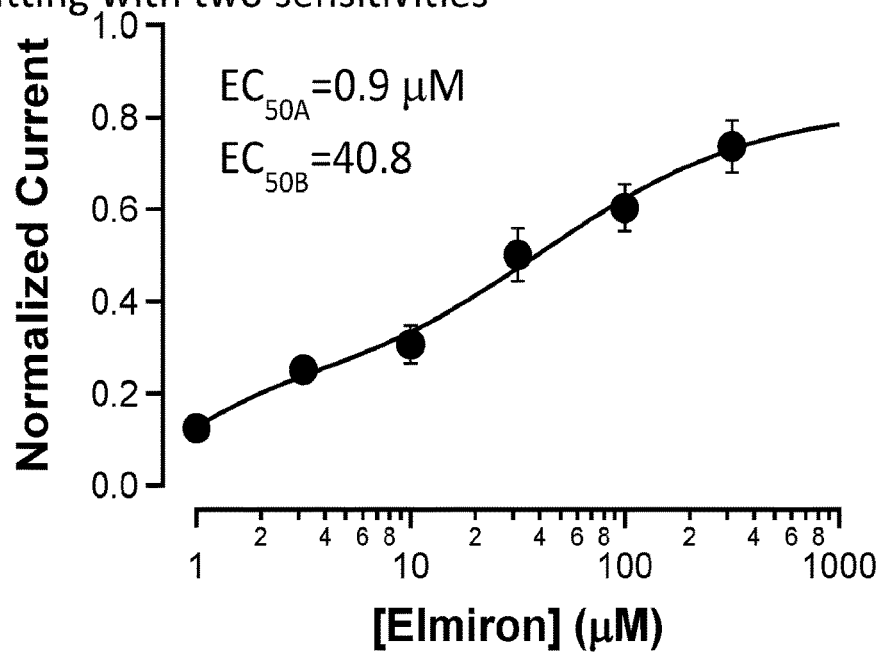
Figure 21:
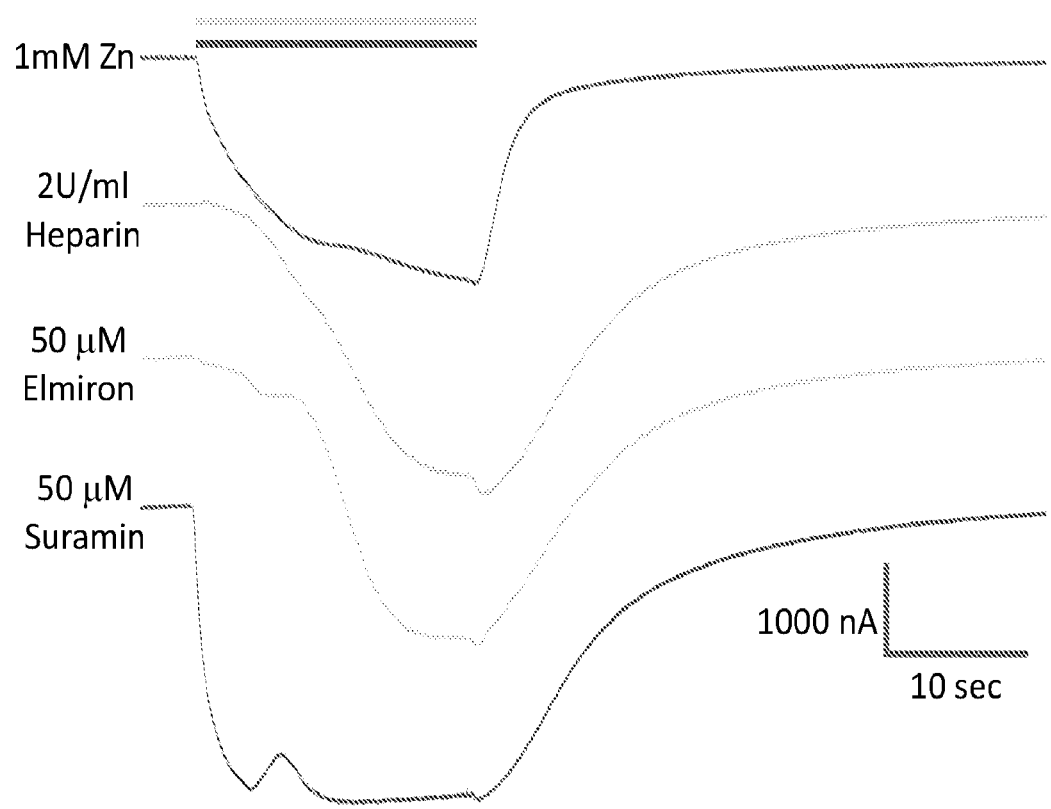
FIG. 21 illustrates, in accordance with the embodiments herein, heparin is an agonist of the human ZACN.
Figure 22:
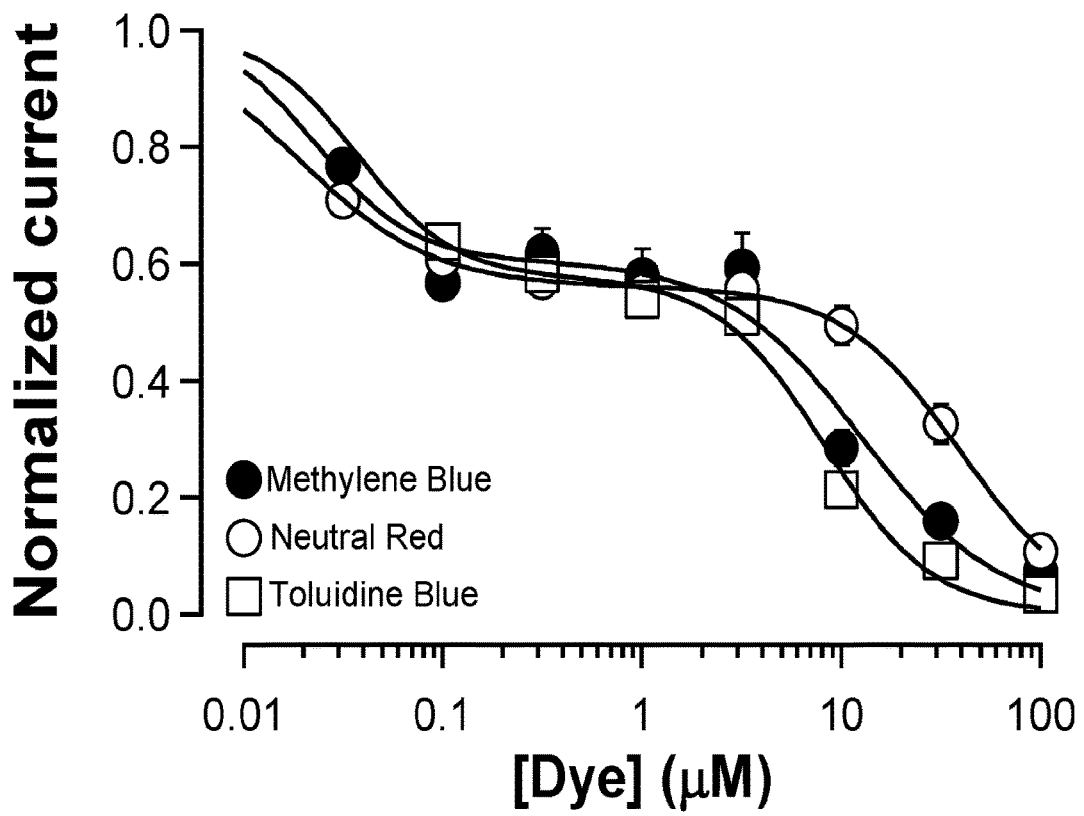
FIG. 22. illustrates, in accordance with the embodiments herein, three blue/red dyes are antagonists to inhibit the human ZACN. Methylene blue used in this study has been used in clinical trial to treat Alzheimer's disease patients. It also has anti-inflammatory effect.
Figure 22:
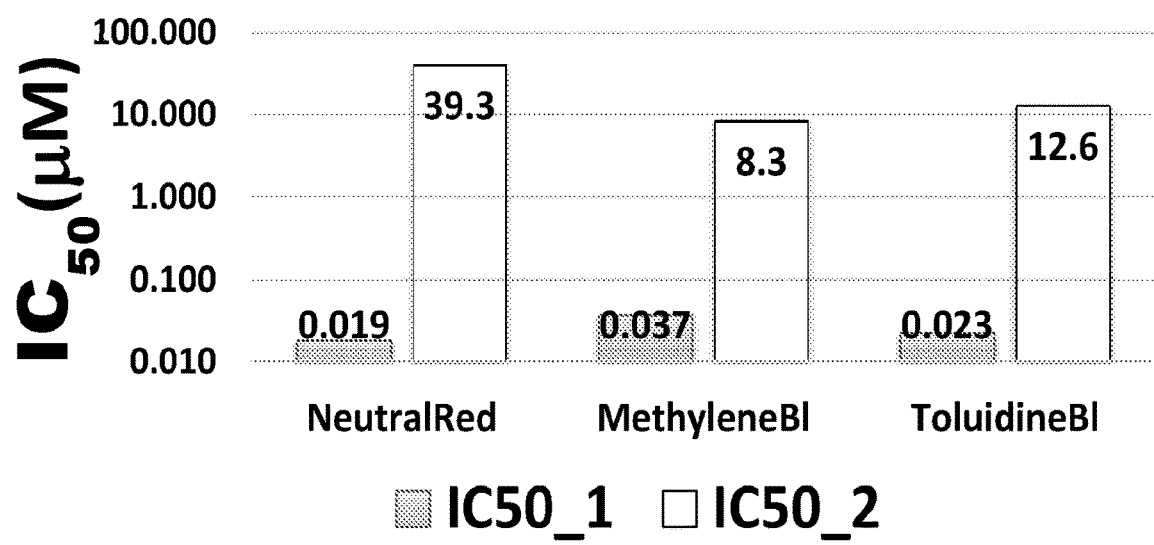

FIG. 12 illustrates the purinergic P2X antagonist, Evans blue, is an efficacious agonist to activate the human ZACN. FIG. 13 illustrates the purinergic P2X antagonist, Trypan blue, is an efficacious agonist to activate the human ZACN. FIG. 14 illustrates the purinergic P2X antagonist, NF-157, is an efficacious agonist to activate the human ZACN. FIG. 15 illustrates the purinergic P2X antagonist, NF-279, is an efficacious agonist to activate the human ZACN. FIG. 16 illustrates the purinergic P2X antagonist, NF-110, is an agonist to activate the human ZACN. FIG. 17 illustrates, in accordance with the embodiments herein, the purinergic P2X antagonist, NF-023, is an agonist to activate the human ZACN. FIG. 18 illustrates the purinergic P2X antagonist, NF-449, is an agonist to activate the human ZACN. It has a small high sensitivity component, saturated at 1 μM. FIG. 19 illustrates five other blue dyes are agonists of the human ZACN with various potencies. Among them, nitro blue tetrazolium has the highest potency with an $EC_{50}$ of 17 μM. FIG. 20 illustrates heparin analog, pentosane polysulfate is an agonist of the human ZACN. The sodium salt of pentosan polysulfate was used; the compound was plant derived, with little anticoagulant activity, anti-inflammatory, orally active. The pentosan polysulfate was also anti-inflammatory, antiadhesive, and antimetastatic. FIG. 21 illustrates that heparin is an agonist of the human ZACN.

Example 14

Antidepressants' Antagonist Effect on Zinc-Activated Cation Channel (ZACN)

Stage IV oocytes from *Xenopus laevis* were injected with lng of ZACN human mRNA. Prior to recording, oocytes were incubated in the oocyte Ringer's Solution (OR2) with 10 µM D-tubocurarine to inhibit spontaneous channel opening. The oocytes were incubated at 14° C. for three to five days following mRNA injection before recording with two-electrode voltage-clamp. Antidepressant drugs were prepared to the listed concentrations and co-applied with 500 µM or 2 mM $ZnCl_2$, the approximate $EC_{50}$ and $EC_{80}$ $Zn^{2+}$ concentrations for this receptor, to determine whether antagonism was competitive or non-competitive. Current levels in response to drug applications were normalized to the response to the same concentration of zinc in the absence of the drug. Peak current inhibitions were fitted to the Hill equation to derive $IC_{50}$ values.

Figure 23:
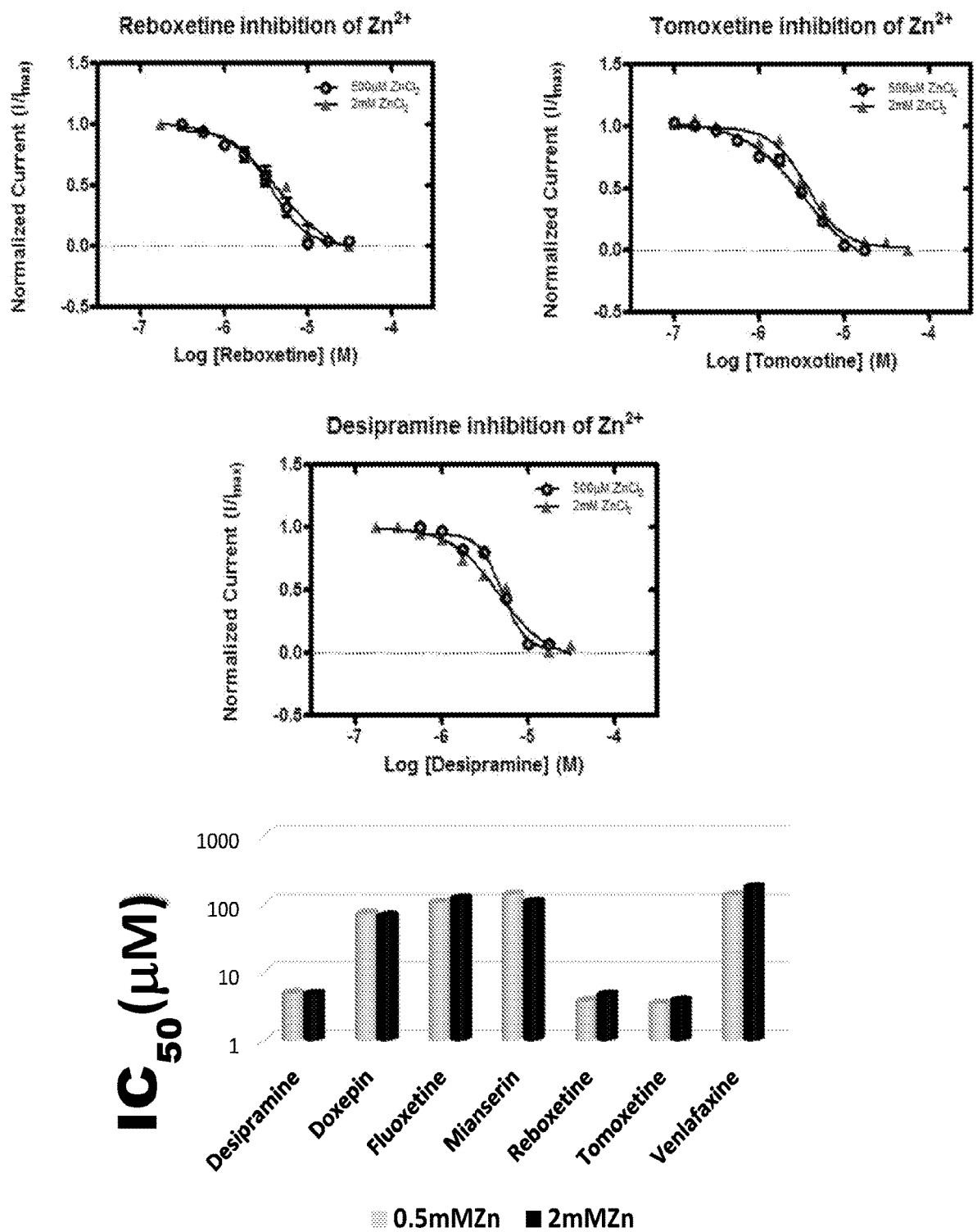
FIG. 23 illustrates, in accordance with the embodiments herein, antidepressants are novel antagonists of human ZACN. Reboxentine, tomoxentine, and desipranine are most potent antagonists of the human ZACN among seven tested antidepressants, with their $IC_{50}$s in clinically relevant concentrations.

As disclosed in FIG. 23, several antidepressant drugs (desipramine, doxepin, fluoxetine, mianserin, reboxetine, tomoxetine, venlafaxine) from five classes acted as antagonists on the ZACN. No significant difference in the $IC_{50}$ values for antagonism of each drug on the currents induced by 500 µM and 2 mM $Zn^{2+}$ was observed, demonstrating that the antagonism is non-competitive. Drug potency varied considerably within classes but the norepinephrine reuptake inhibitors antidepressants appear to be the most potent. Three of the tested drugs, Desipramine, Reboxetine, and Tomoxetine, exhibited lower $IC_{50}$ values for the $Zn^{2+}$-induced current than the other four tested drugs. These results illustrate that ZACN is a novel target for antidepressant action.

Example 15

Generally

In one aspect, the disclosure herein provides a method of diagnosing a disease or condition associated with Treg cells in a subject, comprising providing a tissue cell sample from the subject, incubating the tissue cell sample with one or more antibodies, performing an assay to detect ZACN expression, determining the presence or absence of Treg cells based on the presence or absence of ZACN, and diagnosing the disease or condition based on the presence of Treg cells. In a second aspect, described herein is a method of treating cancer, autoimmune diseases, and inflammatory diseases, comprising modulating the function of ZACN. In one embodiment of this aspect, modulating the function of ZACN increases intracellular calcium in Treg cells by activating the ZACN channel, wherein the increased intracellular calcium in Treg cells activates the Treg cells, and wherein the activated T reg cells regulate a level of immune tolerance. In a third aspect described herein is a method of alleviating organ transplantation rejection, comprising modulating Treg function with ZACN. In a fourth aspect described herein is a treatment for depression. In fact, depression has been linked to autoimmune disease. In one embodiment, this link may be due to use of antidepressants that blocking ZACN function and influencing immune tolerance.

ZACN mRNA is expressed in different human brain regions, such as hippocampus, striatum, amygdala, and thalamus, as well as in other tissues, such as lung, liver, pancreas. Thus, ZACN is expressed in the brain regions important for cognitive function. However, until now, the physiological function of this ligand-gated ion channel has not been explored. In recent years, more and more genomes have been sequenced. Now, NCBI database has listed 164 ZACN genes, mostly predicted, in mammals, including some rodents, suggesting that it is an evolutionarily new gene with potential novel physiological functions. However, ZACN gene does not exist in rat and mouse.

In one embodiment, disclosed herein is fluorescent immunostaining of the human thymus for expression of ZACN protein. The ZACN protein is expressed in a small fraction of human thymus cells. The co-immunostaining results described are reveal that the ZACN+ cells are a subset of the CD4+ cells. The ZACN+ immunostaining overlaps with the FOXP3+ immunostainings, illustrating that this channel is specifically expressed in the regulatory T cells (Treg) in the immune system.

As known to a skilled artisan in the art, T cells are the lymphocytes matured in the thymus. They play a central role in cellular immunity. They differ from other cells by the presence of T-cell receptor (TCR) on the cell surface. T cells can be further divided into subpopulations: T helper cells, cytotoxic T cells, memory T cells, and regulatory T cells. Cell-specific proteins are used as markers for different T cell subtypes. While all T cells express CD3 (components of TCR complex), T helper cells express CD4, and cytotoxic T cells express CD8. CD4+ T cells can be further divided into T helper cells (Th1, Th2, Th17), regulatory T cells (Treg), and naive T cells. Human naive CD4+ T cells express the longest isoform of CD45 (CD45RA), which is lost upon T cell activation. Treg cells belong to a special population of T cells with suppression function to control immune tolerance to self-antigens or foreign antigens. Treg cells are a subset of CD4+ T cells highly expressing the interleukin 2 (IL-2) receptor α-chain (CD25). However, CD25 is also up-regulated in all activated T cells. Thus, only those cells with CD4+CD25$^{high}$ are considered to be Treg cells. Forkhead box P3 (FOXP3) is the most specific marker for Treg. FOXP3 is a transcription factor, which is a master regulator, controlling gene expression of many genes. FOXP3 is essential not only for Treg differentiation and suppressor function, but also for Treg phenotype maintenance and function. Mutations or deficiency of FOXP3 are linked to multi-organ autoimmune diseases. Other markers for Treg include CD127low, or CD39 in a fraction of Treg.

$GABA_A$ receptors, nicotinic receptors and P2X receptors are expressed in the T cells. They play an important role in the modulation of immunological function. Identification of specific expression of ZACN in Treg cells is more interesting. Treg cells play a pivotal role in immune tolerance. Decrease in number or function of these cells is associated with autoimmune diseases. Treg cells accumulate in tumors and are increased in the peripheral blood of tumor patients. Thus, in accordance with embodiments herein, Treg cells can promote tumor growth through suppression of anti-tumor immune response, and help tumor cells to escape from the anti-tumor immune surveillance.

Thus, ZACN as a novel protein expressed in Treg, may be used as a novel Treg cell surface marker. Further, ZACN as a novel protein expressed in Treg, provides a novel means to modulate Treg function in health and disease, particularly in autoimmune diseases and cancer. Treg also find its application in alleviating organ transplantation rejection.

Tregs can be divided into two populations: natural regulatory T cells (nTreg), which differentiate in the thymus, and induced regulatory T cells (iTreg), which differentiate in peripheral lymph organs. The differentiation of nTregs in thymus is promoted by interactions with self-antigens. In contrast, differentiation of iTreg cells is due to the response to non-self-antigens, such as allergens, food, and commensal microbiota, the microorganisms live mostly in gut, but does not affect their host. Since the gut is constantly exposed to different food, and with gut commensal microbiota, the gut-associated lymphoid tissues would have favorable environments for iTreg generation. iTreg can also be induced in vitro from naive CD4+CD25− T cells. The key factors for induction are IL-2 and TGF-beta. In mice, FoxP3 is a specific marker for Treg cells, and TGF-β1 promotes the differentiation of functional Treg cells. However, in humans, the differentiation of Treg cells requires other signals in addition to those controlled by FOXP3. In addition, human Treg populations are heterogeneous. In addition to CD4+ CD25$^{high}$FOXP3+ cells, human Treg cells also include FOXP3−, interleukin-10 producing, type 1 regulatory T cell (Tr1) and TGF-β producing T helper 3 cells (Th3).

Zinc is trace element in the body. In the nervous system, zinc is concentrated in the nerve terminals of glutamatergic neurons, co-released with glutamate, and modify glutamate mediated fast synaptic transmission. Zinc is also important for immune function, especially for T cells. Zinc deficiency can severely influence the immune function. Zinc concentration in the cord blood is correlated to the thymic size, suggesting that zinc is also important in T cell maturation. Many zinc effects are mediated by zinc-finger containing transcription factors or zinc containing thymic hormone, thymulin. Some of the zinc effects are mediated by ZACN in the animals carrying the ZACN gene. Perhaps most mammals have evolved to express ZACN protein in Treg to add another level of control for zinc modulation of immune function.

In one embodiment described herein, ZACN mRNA is expressed in human immune organs. In another embodiment, using immunostaining the inventors demonstrate that ZACN is specifically expressed in the CD4+CD25+ FOXP3+ cells in human immune organs (thymus, lymph nodes, spleen, tonsils) as well as in peripheral blood mononuclear cells. These results suggest that ZACN protein is expressed in the natural regulatory T cells. Interestingly, the induction of Treg in vitro also induced the expression of ZACN, which expression is nearly completely overlapped with FOXP3. Moreover, ZACN is functional in iTreg cells as measured by zinc-induced intracellular calcium increase. In one embodiment, blocking ZACN function inhibited the iTreg suppression function, suggesting ZACN is a novel regulator of Treg function. These novel findings will form the foundation for future in vivo studies, testing its physiological function and implications in health and disease.

In one aspect of the present disclosure, a BLAST search of the human Expressed Sequence Tag (EST) database in the National Center for Biotechnology Information (NCBI) website with the human ZACN mRNA sequence has identified 7 cDNA clones with human ZACN sequences. Four of these clones are from the thymus, showing that the mRNA of human ZACN is expressed in the human thymus cells. In one embodiment, in the NCBI Gene Expression Omnibus (GEO) profile database, the inventors found that ZACN has relatively high expression in immune organs, including thymus, lymph node, and spleen, and immune cells, especially CD4+ T cells (Profile GDS3834/1730/ZACN). This data demonstrated that ZACN was highly co-localized with CD4 and CD25 T cell markers, and FOXP3 regulatory T cell marker, in the human thymus.

In one embodiment, ZACN protein is expressed in a subset of Treg cells and plays an important role in regulating immune function. This was shown from fluorescent immunostaining of the human immune organs, as well as peripheral blood mononuclear cells (PBMCs, FACS analysis) with an anti-ZACN antibody and co-immunostaining with T cell markers.

ZACN is expressed both in nTregs and iTregs. In one embodiment, in vitro induction of iTreg from human naive T cells isolated from the human PBMCs was performed, and the investigators analyzed the expression of ZACN and CD4, CD25, and FOXP3 markers in the iTregs by FACS. Furthermore, the function of ZACN in iTreg cells with CFSE-based Treg suppression assay was tested, and observed the effects of activation/blocking ZACN on iTreg immune suppression function.

The Zinc Activated Cation Channel (ZACN) is a member of the Cys-loop ligand-gated ion channel (LGIC) superfamily that is activated by zinc. The ZACN has been identified in select adult brain areas including the hippocampus, striatum, amygdala, and thalamus. Since the early 90's, nicotinic acetylcholine (nACh) and serotonin (5-HT) type 3, both cationic members of the LGIC superfamily, have been targets for new antidepressant drug development.

In one embodiment, disclosed herein are the effects of antidepressants on the ZACN receptor using the *Xenopus laevis* oocyte expression system and two electrode voltage-clamp. Various antidepressants from the serotonin-norepinephrine reuptake inhibitor (SNRI), selective serotonin reuptake inhibitor (SSRI), norepinephrine reuptake inhibitor (NRI), and tricyclic classes of antidepressants were investigated to study the effect of antidepressants. Most antidepressants tested possessed an antagonistic effect on the zinc-activated current. The inhibitory effects were noncompetitive, because $IC_{50}$ values had no significant difference for the current activated by 500 μM and 2 mM $ZnCl_2$. Thus, ZACN is a new target for some antidepressants.

In one embodiment, Nitro Blue Tetrazolium (NBT) is a selective agonist of ZACN receptor. NBT has no agonist or antagonist effect on any of the other Cys-loop receptor sub-families ($GABA_{A/C}$, Glycine, nACh, and 5HT type 3 receptors). The $EC_{50}$ value of NBT (17.04±0.69 μM) is approximately 100 fold lower than that of $ZnCl_2$ (1645±56 μM) in activating ZACN. ZACN Recovery from NBT activation is much slower than activation by $ZnCl_2$. The $EC_{50}$ value for $ZnCl_2$ on ZACN expressed in *Xenopus* oocytes (1645 μM) is approximately 3 fold greater compared to the $ZnCl_2$ $EC_{50}$ value for ZACN expressed in HEK cells (540 μM).

Example 16

ZACN is a Novel Target of Purinergic Agonists and Antagonists

As further disclosed herein, the inventors have found that ZACN is a novel target of purinergic agonists and antagonists. Specifically, the P2X receptor agonist, ATP, is an antagonist of zinc induced current on ZACN, whereas P2X antagonists, suramin and Evans blue, are agonists for ZACN. The inventors have also found that ATP is a positive allosteric modulator of suramin-induced current on ZACN.

Extracellular ATP can serve as an immune transmitter in the immune synapse between antigen presenting cells and T cells. Extracellular ATP released from injured cells is also a danger signal to initiate the immune response and inflammation. Currently known extracellular ATP receptors are P2X (ion channels) and P2Y (G-protein-linked receptors) receptors. In one embodiment, the present disclosure provides a novel mechanism of ATP action through ZACN functional regulation. In another embodiment, the present disclosure provides a novel drug target to develop new therapeutic drugs to treat autoimmune diseases, inflammation, transplantation rejection, and cancer therapy.

In one embodiment, the current finding that ZACN is a novel target of purinergic agonist and antagonists would provide a novel mechanism to regulate immune function and inflammation by endogenous extracellular ATP. As is known to a skilled artisan, rats and mice do not have the ZACN gene. Thus the current results on ZACN would solve the mystery of the major discrepancy between mouse and human inflammation response—that is, why some successful mouse studies of inflammation fail in human clinical trials.

In one embodiment, the present disclosure provides experimental evidence to show that extracellular ATP can modulate ZACN function in a complex way, depending on the agonist used for ZACN activation. It provides a novel way to understand immune regulation and inflammation through extracellular ATP.

In various embodiments, the present disclosure describes agonists, antagonists, positive and negative allosteric modulators for ZACN. In one embodiment, these compounds are a new generation of anti-inflammatory drugs, or could be used for the treatment of autoimmune diseases, transplantation rejection, and cancer.

Example 17

Materials and Methods cDNA and cRNA Preparation:

The cDNA encoding wild type, human ZACN was purchased from OpenBiosystems, and cloned into the pGEMHE vector in the T7 orientation. For cRNA synthesis, cDNA templates were PCR amplified using primers that cover the M13 forward and reverse regions and high fidelity Phusion DNA polymerase (New England Biolab, Ipswich, Mass., USA). PCR products were then purified and served as templates for cRNA synthesis. cRNAs were transcribed by T7 RNA polymerase (Promega, Madison, Wis., USA) using standard in vitro transcription protocols. After digestion of the DNA template by RNase-free DNase I, cRNAs were purified and resuspended in diethyl pyrocarbonate (DEPC)-treated water. cRNA integrity was examined on a 1% agarose gel, and cRNA concentration was determined by optical density measurements at 260 nm using an Eppendorf Biophotometer.

Oocyte Preparation and Injection:

Oocytes were harvested from female *Xenopus laevis* (*Xenopus* I, Ann Arbor, Mich., USA), using the protocol "*Xenopus* Care and Use" approved by the Institutional Animal Care and Use Committee of the St. Joseph's Hospital and Medical Center. Stage VI oocytes were selected and incubated at 16° C. before injection. Micropipettes for injection were pulled from borosilicate glass (Drummond Scientific, Broomall, Pa., USA) on a Sutter P87 horizontal puller, and the tips were cut with forceps to ≈40 µm in diameter. cRNAs encoding ZACN was drawn up into the micropipette and injected into oocytes with a Nanoject micro-injection system (Drummond Scientific) in a total volume of ~60 nl and total cRNA of ~20 ng for each oocyte.

Two-Electrode Voltage-Clamp:

Two to 5 days after injection, oocytes expressing ZACN were placed in a home-made, small volume chamber and a 16-channel manifold, continuously perfused with oocyte Ringer's solution (OR2), which consisted of (in mM) 92.5 NaCl, 2.5 KCl, 1 CaCl2, 1 MgCl2 and 5 HEPES, pH 7.5. ValveLink 16 computer-controlled perfusion system was used to switch solutions between the OR2 and a test solution. The perfusion chamber was grounded through an agar salt bridge to avoid alterations in junction potential between the Ag/AgCl grounding electrode and solution when solution/drug changes occurred. Oocytes were voltage-clamped at −70 mV to measure agonist-induced currents using an AxoClamp 900A amplifier (Axon Instruments, Foster City, Calif., USA). The current signal was low-pass filtered at 20 Hz with the built-in 4-pole low-pass Bessel filter and digitized at 100 Hz with a Digidata1440a and pClamp 10 software (Molecular Devices).

Drug Preparation:

Zinc chloride, suramin, blue dyes, red dye, and ATP were purchased from Sigma Aldrich (St. Louis, Mo., USA). Antidepressants and other purinergic antagonists were purchased from R&D systems (Tocris, Minneapolis, Minn., USA). Stock solutions were prepared with water, and stored in aliquots at −20° C. before use.

Data Analysis:

For each oocyte, concentration-inhibition curves for drug-induced inhibition of zinc-activated current responses or concentration response curves for agonist-induced current of the ZACN were fit to the Hill equation using least squares methods (Prism 6.0, GraphPad Software, Inc., San Diego, Calif., USA) to derive IC50 or EC50 values (the concentration required for inducing a half maximal current), Hill coefficients (the slope factor), and maximum current levels in absolute terms. Current levels in each oocyte were normalized to the maximum current in the absence of the inhibitor, allowing normalized data to be averaged across multiple oocytes and to be fit again to the Hill equation. All data are presented as mean±SEM (standard error).

Similar experiments and data analysis was done for the red and blue dyes, such as, pentosan polysulfate, Evans blue, trypan blue.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

What is claimed is:

1. A method of activating the function of human Zinc Activated Cation Channel (ZACN) in a subject comprising administering to the subject a pharmaceutically effective dosage of suramin; and activating the function of human ZACN in the subject.

2. The method of claim 1, wherein the subject is a human.

3. The method of claim 1, wherein activating the function of ZACN regulates immune tolerance in the subject.

4. The method of claim 1, wherein the subject is afflicted with an inflammatory disease.

5. The method of claim 4, wherein activating the function of ZACN regulates inflammation in the subject.

6. The method of claim 1, wherein the subject has undergone or is about to undergo tissue or organ implantation.

7. The method of claim 6, wherein activating the function of ZACN regulates immune tolerance to the tissue or organ implantation in the subject.

8. A method of activating the function of human Zinc Activated Cation Channel (ZACN) in a subject comprising administering to the subject a pharmaceutically effective dosage of suramin and ATP and activating the function of human ZACN in the subject.

* * * * *